(12) United States Patent
Yan et al.

(10) Patent No.: US 11,899,023 B2
(45) Date of Patent: Feb. 13, 2024

(54) QUANTITATION AND IDENTIFICATION OF DIMERS IN CO-FORMULATIONS

(71) Applicant: Regeneron Pharmaceuticals, Inc., Tarrytown, NY (US)

(72) Inventors: Yuetian Yan, Chappaqua, NY (US); Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/982,178

(22) Filed: Nov. 7, 2022

(65) Prior Publication Data

US 2023/0070556 A1  Mar. 9, 2023

Related U.S. Application Data

(63) Continuation of application No. 16/750,845, filed on Jan. 23, 2020, now Pat. No. 11,536,725.

(60) Provisional application No. 62/852,591, filed on May 24, 2019, provisional application No. 62/796,794, filed on Jan. 25, 2019.

(51) Int. Cl.
*G01N 33/68* (2006.01)
*G01N 1/28* (2006.01)
*G01N 30/72* (2006.01)
*G01N 33/543* (2006.01)

(52) U.S. Cl.
CPC .......... *G01N 33/6848* (2013.01); *G01N 1/28* (2013.01); *G01N 30/7266* (2013.01); *G01N 33/54366* (2013.01); *G01N 2560/00* (2013.01)

(58) Field of Classification Search
CPC .. G01N 33/6848; G01N 1/28; G01N 30/7266; G01N 33/54366; G01N 2560/00; G01N 30/88; G01N 30/7233; G01N 30/74; G01N 2030/8831; G01N 30/02; G01N 2030/022

See application file for complete search history.

(56) References Cited

U.S. PATENT DOCUMENTS 11,536,725 B2 * 12/2022 Yan ................. G01N 30/88
2005/0161399 A1 7/2005 Dillon et al.
(Continued)

FOREIGN PATENT DOCUMENTS

CN 102162808 A 8/2011
CN 103858003 A 6/2014
(Continued)

OTHER PUBLICATIONS

Basak Kukrer et al: "Mass Spectrometric Analysis of Intact Human Monoclonal Antibody Aggregates Fractionated by Size-Exclusion Chromatography", Pharmaceutical Research, Kluwer Academic Publishers-Plenum Publishers, NL, vol. 27, No. 10, Aug. 3, 2010 (Aug. 3, 2010), pp. 2197-2204 (Year: 2010).*

(Continued)

*Primary Examiner* — David A Vanore
(74) *Attorney, Agent, or Firm* — Kramer Levin Naftalis & Frankel LLP

(57) ABSTRACT

Methods and system for identification of dimer species using online chromatography and electrospray ionization mass spectrometry are provided. Also provided are methods and system for quantitation of heterodimer species using immunoprecipitation and liquid chromatography-mass spectrometry.

8 Claims, 21 Drawing Sheets

(56) References Cited

U.S. PATENT DOCUMENTS

| | | |
|---|---|---|
| 2015/0316515 A1 | 11/2015 | Lauber et al. |
| 2018/0005809 A1 | 1/2018 | Roukes et al. |
| 2020/0132697 A1* | 4/2020 | Yan .................... G01N 33/6854 |
| 2020/0240965 A1* | 7/2020 | Zhang .................... C07K 16/16 |
| 2020/0240998 A1* | 7/2020 | Yan .................... G01N 30/7266 |
| 2020/0240999 A1* | 7/2020 | Wang .................... G01N 33/6848 |
| 2022/0043002 A9* | 2/2022 | Yan .......................... G01N 30/06 |

FOREIGN PATENT DOCUMENTS

| | | |
|---|---|---|
| EP | 3425386 A1 | 1/2019 |
| JP | 2006-208334 A2 | 8/2006 |

OTHER PUBLICATIONS

Basak Kukrer et al: "Mass Spectrometric Analysis of Intact Human Monoclonal Antibody Aggregates Fractionated by Size-Exclusion Chromatography", Pharmaceutical Research, Kluwer Academic Publishers-Plenum Publishers, NL, vol. 27, No. 10, Aug. 3, 2010 (Aug. 3, 2010), pp. 2197-2204.

Pazehoski et al: "Stalking metal-linked dimers", Journal of Inorganic Biochemistry, Elsevier Inc, US, vol. 102, No. 3, Nov. 28, 2007 (Nov. 28, 2007), pp. 522-531.

Gysler J et al: "Utility of isotachophoresis-capillary zone electrophoresis, mass spectrometry and high-performance size-exclusion chromatography for monitoring of interleukin-6 dimer formation", Journal of Chromatography A, Elsevier, Amsterdam, NL, vol. 841, No. 1, May 7, 1999 (May 7, 1999), pp. 63-73.

R. Jeremy Woods et al: "LC-MS characterization and purity assessment of a prototype bispecific antibody", MABS, vol. 5, No. 5, Sep. 1, 2013 (Sep. 1, 2013), pp. 711-722.

Thomas Spreter Von Kreudenstein et al.: "Improving biophysical properties of a bispecific antibody scaffold to aid developability : Quality by molecular design", MABS, vol. 5, No. 5,Sep. 1, 2013 (Sep. 1, 2013), pp. 646-654.

Barzen-Hanson Krista A et al: "Quantitation of carbohydrate monomers and dimers by liquid chromatography coupled with high-resolution mass spectrometry", Carbohydrate Research, Pergamon, GB, vol. 468, Aug. 12, 2018 (Aug. 12, 2018), pp. 30-35.

International Search Report Application No. PCT/2020/014825, Filing Date Jan. 23, 2020, dated Jun. 26, 2020.

Markus Haberger et al., "Rapid characterization of biotherapeutic proteins by size-exclusion chromatography coupled to native mass spectrometry", MABS, 2016, vol. 8, No. 2, pp. 331-339.

Anthony Ehkirch et al., "Hyphenation of size exclusion chromatography to native ion mobility mass spectrometry for the analytical characterization of therapeutic antibodies and related products", Journal of Chromatography B. 2018, vol. 1086, pp. 176-183.

* cited by examiner

- The pull-down fraction contains Fc-fusion protein present in heterodimer
- The flow-through fraction contains Fc-fusion protein present in monomer and homodimer (only 1/10 of the flow-through fraction was used)

FIG. 12
Sample 8
*CW-stressed coformulated protein drug:*
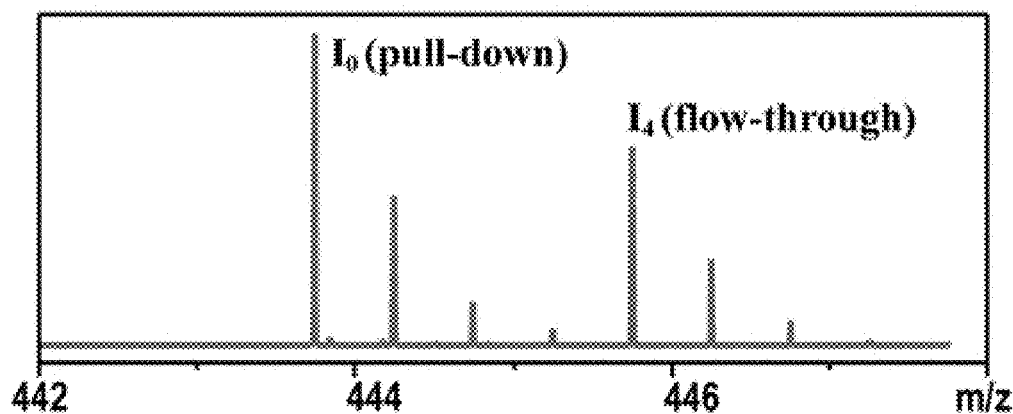
Sample 7
*Negative control: mix individually CW-stressed proteins right before analysis:*
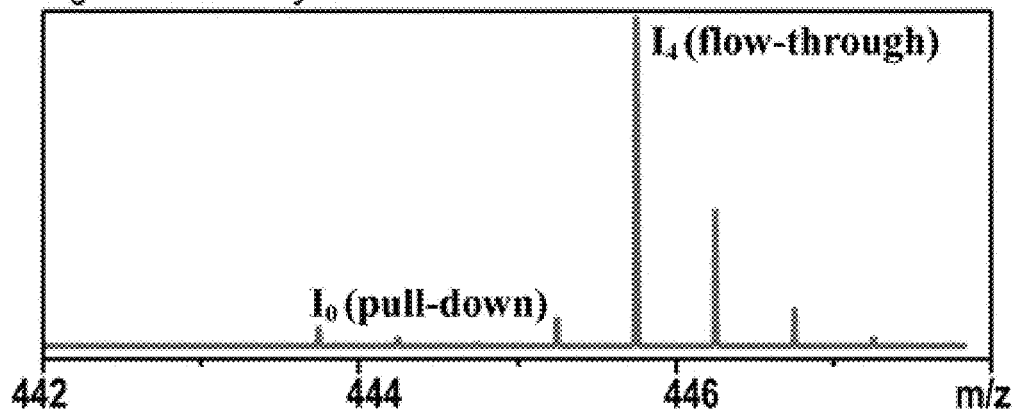

FIG. 18

Converting fusion protein 1$_{heterodimer}$% to Heterodimer% in UV Peak Areas

What is known:
a. 40mg fusion protein 1 and 120mg mAb1
b. M.W. of fusion protein 1 (w/ glycans): 117 kDa
c. CoE of fusion protein 1: 1.15
d. M.W. of mAb1 (w/glycans): 148 kDa
e. CoE of mAb1: 1.37
f. M.W. of heterodimer (w/glycans): 117+148 = 265 kDa
g. CoE of heterodimer: (1.15*97.2+1.37*145)/(97.2+145) = 1.28 [don't consider glycan]
h. The percentage of fusion protein 1 found in heterodimer as determined by MS: a%

Then, the calculated percentage of heterodimer in UV peaks:   $AU \propto (CoE \times Conc)$ $$\frac{(\frac{40mg}{117kDa} \times a\% \times 265kDa) \times 1.28}{(40mg \times 1.15 + 120mg \times 1.37)} \approx 0.55a\%$$

QUANTITATION AND IDENTIFICATION OF DIMERS IN CO-FORMULATIONS

CROSS-REFERENCE TO RELATED APPLICATIONS

This application is a continuation of U.S. patent application Ser. No. 16/750,845, filed on Jan. 23, 2020, which claims priority to and the benefit of U.S. Provisional Patent Application No. 62/852,591, filed on May 24, 2019, and also claims priority to and the benefit of Provisional Patent Application No. 62/796,794, filed on Jan. 25, 2019; the content of which is incorporated herein by reference in its entirety.

FIELD

The invention generally pertains to a method and system for identification of dimer species using online chromatography and electrospray ionization mass spectrometry and quantitation of heterodimer species using immunoprecipitation and liquid chromatography-mass spectrometry.

BACKGROUND

Protein biopharmaceutical products have emerged as important drugs for the treatment of cancer, autoimmune disease, infection and cardiometabolic disorders, and they represent one of the fastest growing product segments of the pharmaceutical industry.

The strategy of co-formulating two or more therapeutic monoclonal antibodies (mAbs) and/or active proteins into one final drug product has gained a lot of popularity recently offering several advantages, including increased efficacy, overall reduced adverse events and improved patient convenience and compliance. Formulating two different mAbs and/or active proteins in a single formulation may be problematic and involves choosing excipients and conditions that may represent a compromise. In addition to challenges for formulation development, co-formulated drugs also present significant challenges for analytical characterization. For example, differentiation and quantitation of different dimer forms present in a co-formulated drug under normal storage or stressed conditions may be challenging and often cannot be achieved by traditional methods such as size exclusion chromatography.

Protein biopharmaceutical products including co-formulated preparations must meet very high standards of purity. Thus, it may be important to monitor any impurities in the co-formulated drug at different stages of drug development, production, storage and handling. Analytical methods for assays for characterization should display sufficient accuracy and resolution to detect and quantify the desired product. Direct analysis can require isolation of the product in a sufficiently large amount for the assay, which is undesirable and has only been possible in selected cases.

There is a long felt need in the art for a method and/or system for characterizing the co-formulated preparations.

SUMMARY

Growth in the development, manufacture and sale of protein biopharmaceutical products has led to an increasing demand for characterizing the protein biopharmaceutical along with possible impurities. Development of stable co-formulated preparations pose an additional challenge since it requires determination of stability and degradation of the individual proteins present in the antibody mixture. Such a determination is often difficult due to the large number of proteins in the formulation, formation of heterodimer species, homodimer species and similarities between such proteins.

Exemplary embodiments disclosed herein satisfy the aforementioned demands by providing methods and/or system for identifying dimer species and/or quantifying a heterodimer species.

This disclosure, at least in part, provides a method for identifying a dimer species. In one exemplary embodiment, the method for identifying a dimer species comprises contacting a sample including the dimer species to a chromatographic system with a chromatography resin, washing said resin using a mobile phase to provide an eluent including the dimer species, and identifying the dimer species in said eluent using an electrospray ionization mass spectrometer.

In one aspect of this embodiment, the method for identifying a dimer species can comprise a chromatographic system with a size exclusion chromatography resin In one aspect of this embodiment, the method for identifying a dimer species can comprise coupling an electrospray ionization mass spectrometer to a chromatographic system with a chromatography resin.

In one aspect of this embodiment, the method for identifying a dimer species can comprise coupling an electrospray ionization mass spectrometer to a chromatographic system having a size-exclusion chromatography resin.

In one aspect of this embodiment, the method for identifying a dimer species can comprise an electrospray ionization mass spectrometer operating under native conditions.

In one aspect of this embodiment, the method for identifying a dimer species can comprise a nano-electrospray ionization mass spectrometer.

In one aspect of this embodiment, the method for identifying a dimer species can comprise a nano-electrospray ionization mass spectrometer operating under native conditions.

In one aspect of this embodiment, the method for identifying a dimer species can comprise at least one splitter with at least three paths to couple an electrospray ionization mass spectrometer to a chromatographic system with a resin.

In one aspect of this embodiment, the method identifying a dimer species can comprise at least one splitter with at least three paths to couple an ultraviolet detector to the chromatographic system with a resin.

In one aspect of this embodiment, the method for identifying a dimer species can comprise at least one splitter with at least three paths to couple an ultraviolet detector and electrospray ionization mass spectrometer to a chromatographic system with a resin.

In one aspect of this embodiment, the method for identifying a dimer species can comprise at least one splitter with at least three paths to couple an electrospray ionization mass spectrometer to a chromatographic system with a size exclusion chromatography resin.

In one aspect of this embodiment, the method for identifying a dimer species can comprise at least one splitter with at least three paths to couple an ultraviolet detector to the chromatographic system with a size exclusion chromatography resin.

In one aspect of this embodiment, the method for identifying a dimer species can comprise at least one splitter with at least three paths to couple an ultraviolet detector and electrospray ionization mass spectrometer to a chromatographic system with a size exclusion chromatography resin.

In one aspect of this embodiment, the method for identifying a dimer species can comprise washing a resin using the mobile phase to provide an eluent including the dimer species, wherein the eluent can be introduced in an ultraviolet detector through at least one splitter with at least three paths, at a flow rate of about 0.2 mL/min to about 0.4 mL/min.

In one aspect of this embodiment, the method for identifying a dimer species can comprise a mobile phase comprising a volatile salt.

In one aspect of this embodiment, the method for identifying a dimer species can comprise a mobile phase comprising ammonium acetate.

In one aspect of this embodiment, the method for identifying a dimer species can comprise washing a resin with the mobile phase with a flow rate of about 0.2 mL/min to about 0.4 mL/min.

In one aspect of this embodiment, the method for identifying a dimer species can comprise a mobile phase with a pH of about 6.8.

In one aspect of this embodiment, the method for identifying a dimer species can comprise a sample including the dimer species in an amount of about 10 μg to about 100 μg.

In one aspect of this embodiment, the method for identifying a dimer species can comprise a dimer species including an antibody.

In one aspect of this embodiment, the method for identifying a dimer species can comprise a dimer species including a fusion protein.

In one aspect of this embodiment, the method for identifying a dimer species can comprise an electrospray ionization mass spectrometer with a flow rate of about 10 nL/min to about 50 nL/min.

In one aspect of this embodiment, the method for identifying a dimer species can comprise an electrospray ionization mass spectrometer with a spray voltage of an electrospray is about 0.8 kV to about 1.5 kV.

In one aspect of this embodiment, the method for identifying a dimer species, wherein the dimer species can be a homodimer species.

In one aspect of this embodiment, the method for identifying a dimer species, wherein the dimer species can be a heterodimer species.

In one aspect of this embodiment, the method for identifying a dimer species can comprise contacting a sample including the dimer species to a chromatographic system with a chromatography resin, wherein the sample can comprise protein monomers.

This disclosure, at least in part, provides a system comprising a chromatographic column having a chromatography resin. In one exemplary embodiment, the system comprises a chromatographic column having a chromatographic resin, wherein the chromatographic column can be capable of receiving a mobile phase and a sample including a protein, and an electrospray ionization mass spectrometer.

In one aspect of this embodiment, the system can comprise a chromatographic column having a size exclusion chromatography resin.

In one aspect of this embodiment, the system can comprise an electrospray ionization mass spectrometer capable of being coupled to said chromatographic column.

In one aspect of this embodiment, the system can comprise an electrospray ionization mass spectrometer capable of being run under native conditions.

In one aspect of this embodiment, the system can comprise a nano electrospray ionization mass spectrometer.

In one aspect of this embodiment, the system can comprise a chromatographic column capable of being coupled to a mass spectrometer using a splitter with at least three paths.

In one aspect of this embodiment, the system can comprise a chromatographic column capable of being coupled to an ultraviolet detector using a splitter with at least three paths.

In one aspect of this embodiment, the system can comprise a chromatographic column capable of being coupled to an ultraviolet detector and a mass spectrometer using a splitter with at least three paths.

In one aspect of this embodiment, the system can be capable of identifying a dimer species.

This disclosure, at least in part, provides a method for quantifying a heterodimer species in a sample comprising a first protein and a second protein, said method comprising immobilizing an antibody specific to the first protein on a solid surface, incubating the sample with said antibody, capturing a precipitated sample, collecting a flow through, treating the precipitated sample with a first compound, treating the flow through with a second compound, mixing the treated precipitated sample and at least a portion of the treated flow through to form a mixture, and analyzing the mixture using a liquid chromatography coupled to a mass spectrometer to quantify the heterodimer species in the sample.

In one aspect of this embodiment, the method for quantifying a heterodimer species in a sample comprising a first protein and a second protein can comprise immobilizing an antibody specific to the first protein on a solid surface, wherein the first protein can be a monoclonal antibody.

In one aspect of this embodiment, the method for quantifying a heterodimer species in a sample comprising a first protein and a second protein can comprise immobilizing an antibody specific to the first protein on a solid surface, wherein the solid surface comprises magnetic beads.

In one aspect of this embodiment, the method for quantifying a heterodimer species in a sample comprising a first protein and a second protein can comprise immobilizing an antibody specific to the first protein on a solid surface, wherein the solid surface comprises streptavidin.

In one aspect of this embodiment, the method for quantifying a heterodimer species in a sample comprising a first protein and a second protein can comprise immobilizing an antibody specific to the first protein on a solid surface and capturing a precipitated sample, wherein the precipitated sample includes the heterodimer species bound to the antibody specific to the first protein on a solid surface.

In one aspect of this embodiment, the method for quantifying a heterodimer species in a sample comprising a first protein and a second protein can comprise immobilizing an antibody specific to the first protein on a solid surface and capturing a precipitated sample, wherein the precipitated sample comprises of the heterodimer species bound to the antibody specific to the first protein on a solid surface.

In one aspect of this embodiment, the method for quantifying a heterodimer species in a sample comprising a first protein and a second protein can comprise immobilizing an antibody specific to the first protein on a solid surface, capturing a precipitated sample, re-suspending the precipitated sample and heating the re-suspended precipitated sample.

In one aspect of this embodiment, the method for quantifying a heterodimer species in a sample comprising a first protein and a second protein can comprise immobilizing an antibody specific to the first protein on a solid surface, capturing a precipitated sample and collecting a flow through.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the flow through with a first compound In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, wherein the first compound can be an isotope of the second compound.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, and mixing the treated precipitated sample and at least a portion of the treated flow through to form a mixture.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, and digesting the mixture.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, digesting the mixture, and deglycosyalting the digested mixture.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, digesting the mixture, and analyzing the mixture using a liquid chromatography coupled to a mass spectrometer to quantify the heterodimer species in the sample.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, digesting the mixture, deglycosylating the digested mixture, and analyzing the mixture using a liquid chromatography coupled to a mass spectrometer to quantify the heterodimer species in the sample.

In one aspect of this embodiment, the method for quantifying a heterodimer species in a sample comprising a first protein and a second protein can comprise analyzing using a liquid chromatography coupled to a mass spectrometer to quantify the heterodimer species in the sample, wherein the mass spectrometer can be a tandem mass spectrometer.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, and adding a reducing agent to the treated precipitated sample.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, and adding a reducing agent to the treated flow through.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and about 10% of the treated flow through to form a mixture, and analyzing the mixture using a liquid chromatography coupled to a mass spectrometer to quantify the heterodimer species in the sample.

In one aspect of this embodiment, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and about 10% of the treated flow through to form a mixture, digesting the mixture, and analyzing the mixture using a liquid chromatography coupled to a mass spectrometer to quantify the heterodimer species in the sample.

This disclosure, at least in part, provides a method for quantifying a heterodimer species. In one exemplary embodiment, the method for quantifying a heterodimer species comprises immunoprecipitating the heterodimer species and quantifying the heterodimer species by using a stable isotope labeling method followed by a liquid chromatography coupled to a mass spectrometer.

In one aspect of this embodiment, the method for quantifying a heterodimer species can comprise a heterodimer species including an antibody.

In one aspect of this embodiment, the method for quantifying a heterodimer species can comprise a heterodimer species including a fusion protein.

In one aspect of this embodiment, the method for quantifying a heterodimer species can comprise immunoprecipitating the heterodimer species by using an antibody on a solid surface.

In one aspect of this embodiment, the method for quantifying a heterodimer species can comprise immunoprecipitating the heterodimer species by using an antibody on a solid surface, wherein the antibody can bind to a protein from the heterodimer.

In one aspect of this embodiment, the method for quantifying a heterodimer species can comprise using a stable isotope labeling method with an alkylating compound.

In one aspect of this embodiment, the method for quantifying a heterodimer species can comprise using a stable isotope labeling method with an alkylating compound.

In one aspect of this embodiment, the method for quantifying a heterodimer species can comprise performing digestion in addition to using a stable isotope labeling method.

BRIEF DESCRIPTION OF THE DRAWINGS

FIG. 12 shows the mass to charge ratios of the pull-down and flow-through fractions obtained for cool white stressed co-formulation and a negative sample according to an exemplary embodiment.

FIG. 18 shows the calculations for converting fusion protein 1 heterodimer % to heterodimer %, wherein the quantitation of a heterodimer comprising fusion protein 1 was performed according to an exemplary embodiment.

DETAILED DESCRIPTION

Figure 1:
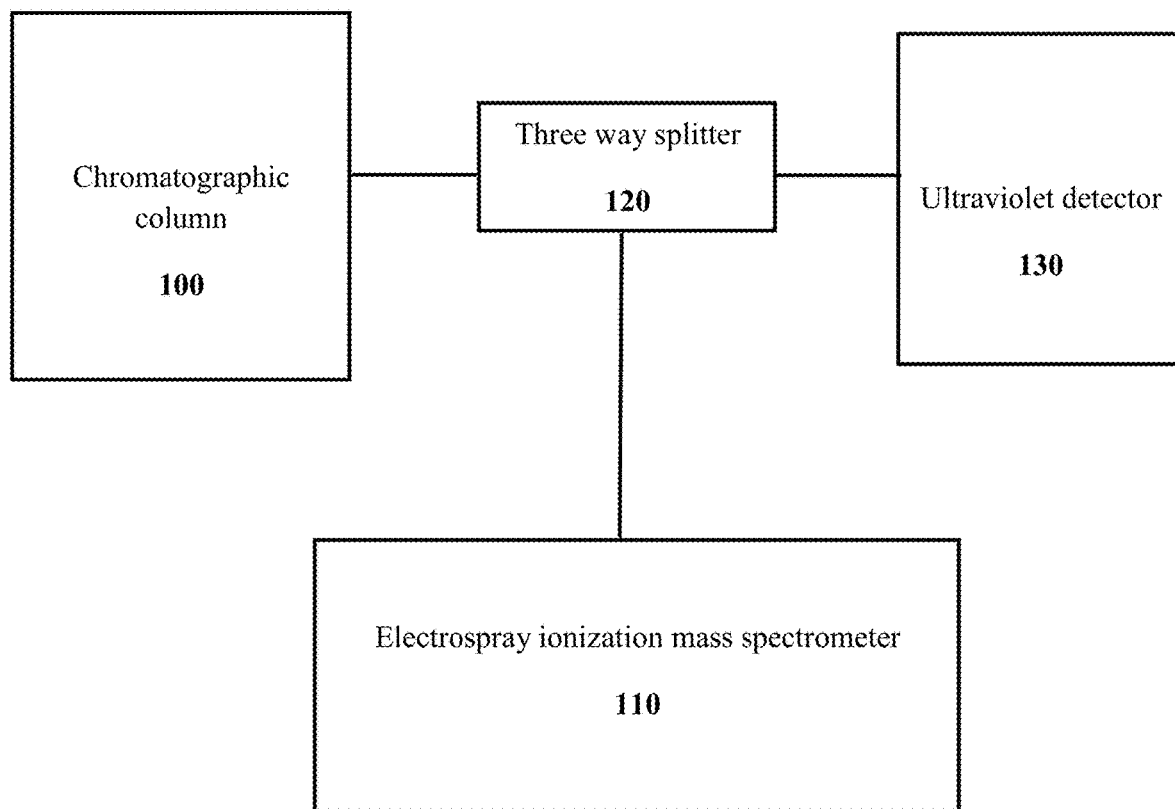
FIG. 1 shows an exemplary embodiment of a system capable of identifying dimer species.

Identification and quantification of proteins in protein biopharmaceutical products may be very important during the production and development of a product. The analysis of impurities in any protein biopharmaceutical product may be imperative into developing a safe and effective product. Hence, a robust method and/or workflow to characterize the impurities may be beneficial.

Most biopharmaceutical products may comprise a single protein. In some instances, multiple proteins directed to a single target or multiple targets administered in combination may improve their diagnostic or therapeutic indication and efficacy. Development of such co-formulated preparations are becoming increasingly popular dosage forms (Svend Havelund et al., *Investigation of the Physico-Chemical Properties that Enable Co-Formulation of Basal Insulin Degludec with Fast-Acting Insulin Aspart*, 32 PHARMACEUTICAL RESEARCH 2250-2258 (2015); Sanjay Kalra & Yashdeep Gupta, *Injectable Coformulations in Diabetology*, 6 DIABETES THERAPY 101-111 (2015); Ryzodeg, EUROPEAN MEDICINES AGENCY-FIND MEDICINE-RAXONE, https://www.ema.europa.eu/en/medicines/human/EPAR/ryzodeg (last visited Jan. 17, 2019)).

The development of co-formulated preparations, however, has some challenges, since it requires studying the potential pharmacodynamics interactions, potential pharmacokinetic interactions, potential for toxicological interactions, potential for changes in the levels or activity of endogenous, and potential for impairing the efficacy of one of the drugs (Claudia Mueller, Ulrike Altenburger & Silke Mohl, *Challenges for the pharmaceutical technical development of protein coformulations*, 70 JOURNAL OF PHARMACY AND PHARMACOLOGY 666-674 (2017)). The manufacture of stable co-formulated preparation may also require additional efforts to ensure the stability of the two more proteins at various steps of the manufacturing.

During storage, transport and administration, the final co-formulated products may get exposed to light, heat and oxygen and cause aggregation (high molecular weight species homodimer(s) and/or heterodimer(s)), charge pattern, fragmentation, chemical modifications (e.g. oxidation, deamidation), etc.

A good analytical method performance and sensitivity are crucial to ensure high quality and safety of the final co-formulated product. However, the analytical approach for the development and evaluation of co-formulated preparations may be significantly challenging and complex than approach applied for formulations comprising a single protein as an active pharmaceutical ingredient. This may become challenging as certain standard methods employed for a formulation comprising a single protein may not always be capable of differentiating proteins in the co-formulated preparations.

One of the methods includes use of size exclusion chromatography (SEC) for characterizing biomolecular aggregation and fragmentation in the biotech industry (Hong Paule et al., *Size-Exclusion Chromatography for the Analysis of Protein Biotherapeutics and their Aggregates*, 35 JOURNAL OF LIQUID CHROMATOGRAPHY AND RELATED TECHNOLOGY 2923-2950 (2012)). The separation of molecules by SEC relies on the differential interaction of molecules with a controlled porous structure on a stationary phase. As SEC uses buffer conditions that preserve the native structure of proteins in solution, it permits characterization of biomolecules without disturbing their native conformation. Further, among the various detection modes that may be coupled with SEC, mass spectrometry (MS) allows for the precise and accurate identification of individual components in complex samples. The combination of SEC and MS has been reported previously, including the collection of SEC peaks followed by direct infusion MS (Başak Kükrer et al., *Mass Spectrometric Analysis of Intact Human Monoclonal Antibody Aggregates Fractionated by Size-Exclusion Chromatography*, 27 PHARMACEUTICAL RESEARCH 2197-2204 (2010); François Debaene et al., *Innovative Native MS Methodologies for Antibody Drug Conjugate Characterization: High Resolution Native MS and IM-MS for Average DAR and DAR Distribution Assessment*, 86 ANALYTICAL CHEMISTRY 10674-10683 (2014)) or online SEC-MS (Khaja Muneeruddin et al., *Characterization of Small Protein Aggregates and Oligomers Using Size Exclusion Chromatography with Online Detection by Native Electrospray Ionization Mass Spectrometry*, 86 ANALYTICAL CHEMISTRY 10692-10699 (2014); C. F. Mcdonagh et al., *Engineered antibody-drug conjugates with defined sites and stoichiometries of drug attachment*, 19 PROTEIN ENGINEERING DESIGN AND SELECTION 299-307 (2006)). However, to directly ionize the high flow generated from SEC separation requires harsh ionization conditions that are often incompatible with native MS analysis, thereby limiting the utility of coupling these technologies for the analysis of non-covalent interactions. Further, the sensitivity of the mass spectrometer may suffer from the high salt concentrations used in SEC buffers.

In addition to the identification, quantification of heterodimer(s) formed in the co-formulated product may also raise challenges, since the amount of heterodimer(s) formed needs to evaluated in presence of the protein monomers and any present homodimer(s).

Considering the limitations of existing methods, effective and efficient methods for identification and quantification of dimer species was developed.

Unless described otherwise, all technical and scientific terms used herein have the same meaning as commonly understood by one of ordinary skill in the art to which this invention belongs. Although any methods and materials similar or equivalent to those described herein may be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure provides a method for identifying dimer species in a co-formulated preparation.

As used herein, a "co-formulated preparation" includes two or more active pharmaceutical ingredients in a single dosage form. This dosage form can be used to treat, prevent, or ameliorate a certain disease condition by targeting different molecular targets and obtain an overall improved medical condition of the patient due to additive and/or synergistic effects as compared to the single dug(s) alone (Claudia Mueller, Ulrike Altenburger & Silke Mohl, *Challenges for the pharmaceutical technical development of protein coformulations*, 70 JOURNAL OF PHARMACY AND PHARMACOLOGY 666-674 (2017)). Some of the advantages include increased efficacy compared to a single drug, overall reduction of adverse event, improvement of patient convenience and compliance (increased patient adherence, simplified patient guidance and education), reduction in health care costs (manufacture and purchase), easier supply processes, and new product opportunities within life-cycle management of existing marketed products.

In some exemplary embodiments, the two or more active pharmaceutical ingredients can be proteins.

In some exemplary embodiments, the co-formulated preparation can comprise at least two proteins.

In some exemplary embodiments, the co-formulated preparation can comprise at least three proteins.

As used herein, the term "protein" includes any amino acid polymer having covalently linked amide bonds. Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a review discussing biotherapeutic proteins and their production, see Ghaderi et al., "Production platforms for biotherapeutic glycoproteins. Occurrence, impact, and challenges of non-human sialylation," (BIOTECHNOL. GENET. ENG. REV. 147-175 (2012)). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins.

In some exemplary embodiments, the protein can be an antibody, a bispecific antibody, a multispecific antibody, antibody fragment, monoclonal antibody, or an Fc fusion protein. In one aspect, the protein is a anti-VEGF protein. In a specific aspect, the VEGF-protein is Aflibercept.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "Fc fusion proteins" as used herein includes part or all of two or more proteins, one of which is an Fc portion of an immunoglobulin molecule, that are not fused in their natural state. Preparation of fusion proteins comprising certain heterologous polypeptides fused to various portions of antibody-derived polypeptides (including the Fc domain)

has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more of one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a single or more than one ligand(s). For example, an Fc-fusion protein is a trap, such as for example an IL-1 trap (e.g., Rilonacept, which contains the IL-1 RAcP ligand binding region fused to the IL-1R1 extracellular region fused to Fc of hIgG1; see U.S. Pat. No. 6,927,004, which is herein incorporated by reference in its entirety), or a VEGF Trap (e.g., Aflibercept, which contains the Ig domain 2 of the VEGF receptor Flt1 fused to the Ig domain 3 of the VEGF receptor Flk1 fused to Fc of hIgG1; e.g., SEQ ID NO:1; see U.S. Pat. Nos. 7,087,411 and 7,279,159, which are herein incorporated by reference in their entirety)

In some exemplary embodiments, the co-formulated preparation can comprise dimer species. In one aspect, the co-formulated preparation can comprise homodimer species. In some other specific exemplary embodiments, the co-formulated preparation can comprise heterodimer species. In another aspect, the co-formulated preparation can comprise homodimer species and heterodimer species.

In some exemplary embodiments, the co-formulated preparation can comprise dimer species as an impurity.

As used herein, the term "impurity" can include any undesirable protein present in the protein biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated; isomerized, mismatched S—S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See European Bioinformatics Institute Protein Information ResourceSlB Swiss Institute of Bioinformatics, EUROPEAN BIOINFORMATICS INSTITUTE DRS-DROSOMYCIN PRECURSOR-DROSOPHILA MELANOGASTER (FRUIT FLY)-DRS GENE & PROTEIN, http://www.uniprot.org/docs/ptmlist (last visited Jan. 15, 2019) for a more detailed controlled vocabulary of PTMs curated by UniProt.

In some exemplary embodiments, dimer species can be identified by contacting a sample including the dimer species to a chromatographic system.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

As used herein, the term "Mixed Mode Chromatography (MMC)" or "multimodal chromatography" includes a chromatographic method in which solutes interact with stationary phase through more than one interaction mode or mechanism. MMC can be used as an alternative or complementary tool to traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings and operation flexibility compared to affinity based methods.

In some exemplary embodiments, the chromatography can be size-exclusion chromatography.

As used herein, the terms "SEC chromatography resin" or "SEC chromatography media" are used interchangeably and can include any kind of solid phase used in SEC which separates the impurity from the desired product (e.g., a homodimer contaminant for a bispecific antibody product). The volume of the resin, the length and diameter of the column to be used, as well as the dynamic capacity and flow-rate can depend on several parameters such as the volume of fluid to be treated, concentration of protein in the fluid to be subjected to the process.

In some exemplary embodiments, the method for identifying dimer species can comprise contacting a sample including the protein biopharmaceutical to a chromatographic system using a mobile phase to provide an eluent including the dimer species; and identifying the protein in said eluent using an electrospray ionization mass spectrometer.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

In some embodiments, the mass spectrometer can be an electrospray-mass spectrometer.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "electrospray infusion setup" refers to an electrospray ionization system that is compatible with a mass spectrometer used for mass analysis of protein. In electrospray ionization, an electrospray needle has its orifice positioned close to the entrance orifice of a spectrometer. A sample, containing the protein of interest, can be pumped through the syringe needle. An electric potential between the syringe needle orifice and an orifice leading to the mass analyzer forms a spray ("electrospray") of the solution. The electrospray can be carried out at atmospheric pressure and provides highly charged droplets of the solution. The electrospray infusion setup can include an electrospray emitter, nebulization gas, and/or an ESI power supply. The setup can optionally be automated to carry out sample aspiration, sample dispensing, sample delivery, and/or for spraying the sample.

In some exemplary embodiments, the electrospray ionization mass spectrometer can be a nano-electrospray ionization mass spectrometer.

The term "nanoelectrospray" or "nanospray" as used herein refers to electrospray ionization at a very low solvent flow rate, typically hundreds of nanoliters per minute of sample solution or lower, often without the use of an external solvent delivery. The electrospray infusion setup forming a nanoelectrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

As used herein, the term "mass analyzer" includes a device that can separate species, that is, atoms, molecules, or clusters, according to their mass. Non-limiting examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

In some exemplary embodiments, mass spectrometry can be performed under native conditions.

As used herein, the term "native conditions" or "native MS" or "native ESI-MS" can include a performing mass spectrometry under conditions that preserve no-covalent interactions in an analyte. For detailed review on native MS, refer to the review: Elisabetta Boeri Erba & Carlo Petosa, *The emerging role of native mass spectrometry in characterizing the structure and dynamics of macromolecular complexes,* 24 PROTEIN SCIENCE 1176-1192 (2015). Some of the distinctions between native ESI and regular ESI are illustrated in table 1 (Hao Zhang et al., *Native mass spectrometry of photosynthetic pigment-protein complexes,* 587 FEBS Letters 1012-1020 (2013)).

TABLE 1

|  | Native ESI | Regular ESI |
| --- | --- | --- |
| Sample Solution | Aqueous solution water, ammonium acetate | Partial organic solution water, formic acid, acetonitrile/Methanol (pH 1-2) |
| Spray Condition | 10-50 nL/min Spray voltage 0.8-1.5 kV Temperatures 20-30° C. | 10-50 nL/min Spray voltage 0.8-1.5 kV Temperatures 20-30° C. |
| Salt Treatment | Offline Desalt | Online/Offline Desalt with RP-HPLC |
| Protein Concentration | 1-10 μM (complex) | <1 μM (subunit) |
| Output Information | Molecular weight of protein complex and subunit Non-covalent interactions Stoichiometry Structure | Molecular weight of a single subunit |

In some exemplary embodiments, the mass spectrometer can be a tandem mass spectrometer.

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information or the fragment ion signal is detectable. Tandem MS have been successfully performed with a wide variety of analyzer combinations. What analyzers to combine for a certain application is determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometer ions produced in the ion source can be trapped, isolated, fragmented, and m/z separated in the same physical device.

The peptides identified by the mass spectrometer can be used as surrogate representatives of the intact protein and their post-translational modifications. They can be used for protein characterization by correlating experimental and theoretical MS/MS data, the latter generated from possible peptides in a protein sequence database. The characterization can include, but is not limited, to sequencing amino acids of the protein fragments, determining protein sequencing, determining protein de novo sequencing, locating post-translational modifications, or identifying post translational modifications, or comparability analysis, or combinations thereof.

As used herein, the term "database" refers to bioinformatic tools which provide the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMS SA (http://www.pubchem.ncbi.nlm.nih.gov/omssa/), X!Tandem (http://www.thegpm.org/TANDEM/), Protein Prospector (http://www. http://prospector.ucsf.edu/prospector/mshome.htm), Byonic (https://www.proteinmetrics.com/products/byonic) or Sequest (http://fields.scripps.edu/sequest).

In some exemplary embodiments, the disclosure provides a method for quantifying a heterodimer species.

In some embodiments, the method for quantifying a heterodimer species in a comprising a first protein and a second protein can comprise immobilizing an antibody specific to the first protein on a solid surface. The antibody specific to the first protein can be prepared using any of the known methods in the literature.

As used herein, the term "solid surface" can include any surface with an ability to bind to an antibody of interest. In some embodiments for a sample comprising a first protein and a second protein, the antibody of interest can be an antibody specific to the first protein. Non-limiting examples of solid surface can include affinity resins, magnetic beads and coated plates with an immobilized protein, such as, avidin, streptavidin, or NeutrAvidin.

In some embodiments, the method for quantifying a heterodimer species can comprise immunoprecipitating the heterodimer species. The immunoprecipitation can be performed by using an antibody immobilized on a solid surface, wherein the antibody can bind to one of many active pharmaceutical ingredients in co-formulated preparation, and wherein the active pharmaceutical ingredients can be proteins.

In some embodiments, the sample comprising a first protein and a second protein can be incubated with an immobilized antibody specific to the first protein on a solid surface. The time of incubation can range from several minutes to several hours.

In some embodiments, the sample comprising a first protein and a second protein incubated with an immobilized antibody specific to the first protein on a solid surface can be pulled down.

In some embodiments, the sample comprising a first protein and a second protein incubated with an immobilized antibody specific to the first protein on a solid surface can be centrifuged. In some specific embodiments, the centrifugation can produce a precipitated sample and a flow through or supernatant.

In some embodiments, the precipitated sample and the flow through can be reduced by using a reducing agent.

As used herein, the term "reducing" refers to the reduction of disulfide bridges in a protein. Non-limiting examples of the reducing agents used to reduce the protein are dithiothreitol (DTT), ß-mercaptoethanol, Ellman's reagent, hydroxylamine hydrochloride, sodium cyanoborohydride, tris(2-carboxyethyl)phosphine hydrochloride (TCEP-HCl), or combinations thereof.

In some embodiments, the precipitated sample and/or flow through can be treated using a compound or compounds. In some specific embodiments, the treatment can include alkylation. In some other specific exemplary embodiments, the treatment can include alkylation of sulfhydryl groups on a protein.

As used herein, the term "treating" or "isotopically labeling" can refer to chemical labeling a protein. Non-selected examples of the methods to chemical labeling a protein include Isobaric tags for relative and absolute quantitation (iTRAQ) using reagents, such as 4-plex, 6-plex, and 8-plex; reductive demethylation of amines, carbamylation of amines, $^{18}$O-labeling on the C-terminus of the protein, or any amine- or sulfhydryl-group of the protein to label amines or sulfhydryl group.

In some embodiments, the precipitated sample and/or flow through can be treated using two distinct compounds, wherein the two compounds are isotopes.

In some embodiments, the precipitated sample and at least a portion of the flow through can be mixed after treating or isotopically labeling them.

In some embodiments, the mixture of the treated or isotopically labeled precipitated sample and at least a portion of the treated or isotopically labeled flow through can be digested.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

Figure 2:
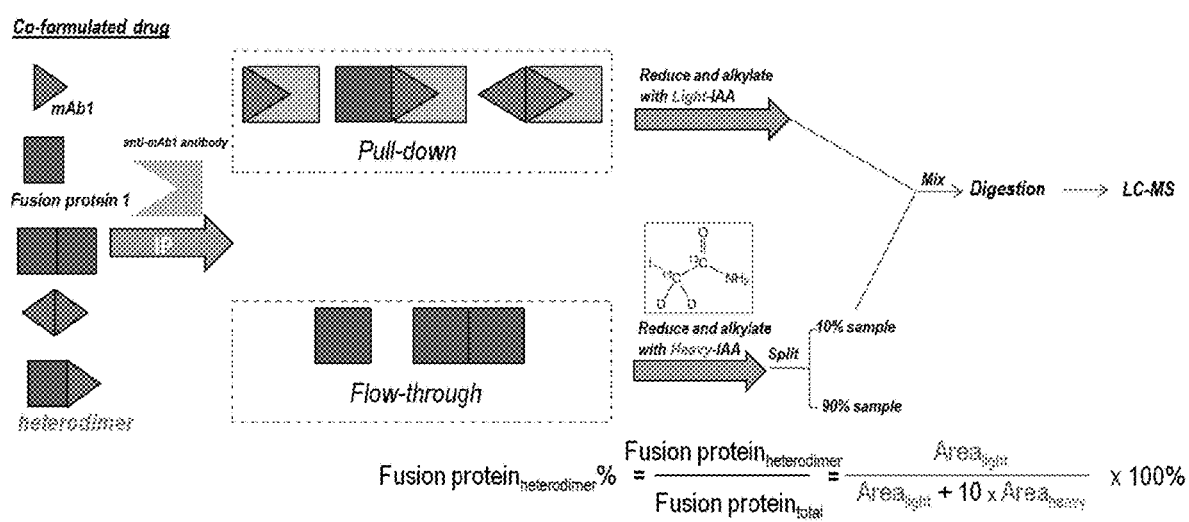
FIG. 2 shows an exemplary embodiment of the method used to quantify heterodimer species in a sample of a co-formulated preparation.

In some embodiments, on digestion of mixture of the treated or isotopically labeled precipitated sample and at least a portion of the treated or isotopically labeled flow through can be analyzed using a liquid chromatography coupled to a mass spectrometer. One such exemplary embodiment is represented on FIG. 2. FIG. 2 shows an exemplary embodiment for a method for quantifying a heterodimer species in a sample comprising a first protein—mAb1 and a second protein—fusion protein 1 in a co-formulated preparation, said method comprising immobilizing an antibody specific to the first protein (anti-mAb1 antibody) on a solid surface, incubating the sample with said antibody, capturing a precipitated sample by pulling down the heterodimer of mAb1 and fusion protein 1, mAb1 monomer and mAb1 dimer, collecting a flow through comprising fusion protein 1 monomer and fusion protein 1 dimer, treating the precipitated sample with a first compound—unlabeled iodoacetamide (IAA), treating the flow through with a second compound—labeled iodoacetamide (IAA), mixing the treated precipitated sample and about 10% of the treated flow through to form a mixture, digesting the said mixture, and analyzing the mixture using a liquid chromatography coupled to a mass spectrometer to quantify the heterodimer species in the sample. During quantitation of the heterodimer species using an exemplary embodiment, non-specific binding of the second protein on incubating the sample with said antibody. Such a non-specific binding could lead to overestimation of the quantity of the heterodimer can occur. Hence, a negative sample can be prepared and the amount of the non-specifically bound second protein can be obtained. An example of one such possibility is shown in FIG. 3.

In some exemplary embodiments, the negative sample can comprise monomers and homodimers of a first protein and a second protein, without the presence of a heterodimer species.

Figure 3:
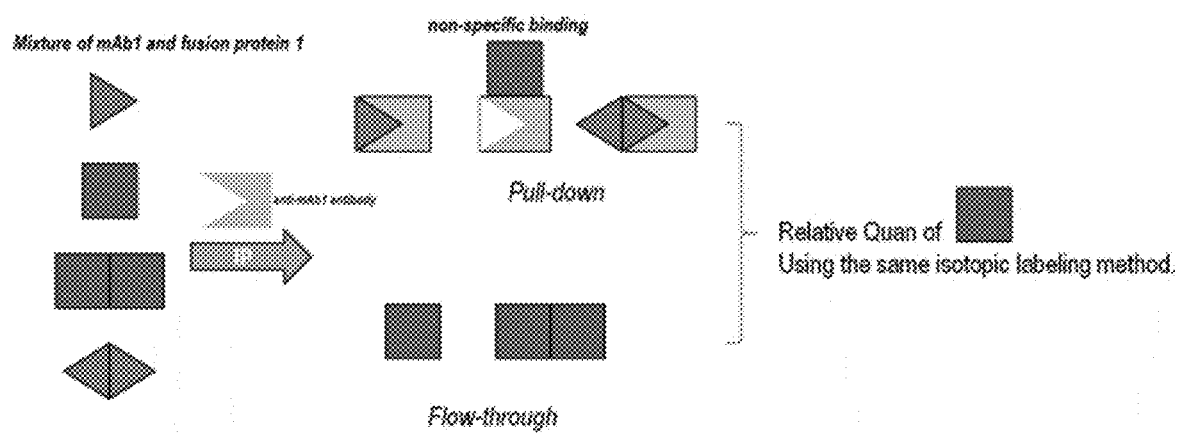
FIG. 3 shows a method for quantifying non-specific binding of a protein to an antibody in a negative sample according to an exemplary embodiment.

FIG. 3 shows an exemplary embodiment for preparing a negative sample. It comprises using a sample comprising monomers and homodimers of a first protein (mAb1) and a second protein (fusion protein 1). This amount of second protein non-specifically bound to the antibody can be quantified by using a method comprising immobilizing an antibody specific to the first protein (anti-mAb1 antibody) on a solid surface, incubating the sample with said antibody, capturing a precipitated sample by pulling down non-specifically bound fusion protein 1, mAb1 monomer and mAb1 dimer, collecting a flow through comprising fusion protein 1 monomer and dimer, treating the precipitated sample with a first compound—unlabeled iodoacetamide (IAA), treating the flow through with a second compound—labeled iodoacetamide (IAA), mixing the treated precipitated sample and about 10% of the treated flow through to form a mixture, and analyzing the mixture using a liquid chromatography coupled to a mass spectrometer to quantify the heterodimer species in the sample.

Exemplary Embodiments

Embodiments disclosed herein provide methods and system for the identification and/or quantification of dimer species.

In some exemplary embodiments, this disclosure provides a method for identification of a dimer species, comprising contacting a sample including the dimer species to a chromatographic system with a chromatography resin, washing said resin using a mobile phase to provide an eluent including the dimer species, and identifying the dimer species in said eluent using an electrospray ionization mass spectrometer.

In some exemplary embodiments, dimer species can be a homodimer species.

In some exemplary embodiments, dimer species can be a heterodimer species.

In some exemplary embodiments, the chromatographic system can include traditional reversed-phased (RP), ion exchange (IEX) or normal phase chromatography (NP).

In some exemplary embodiments, the chromatographic resin can be selected from affinity chromatography resin, anion-exchange resin, cation exchange resin, affinity resin, mixed mode chromatography resin, hydrophobic interaction chromatography resin or size exclusion chromatography resin. In one specific exemplary embodiment, the chromatographic resin can be size exclusion chromatography resin.

In some exemplary embodiments, the electrospray ionization mass spectrometer can be a nano-electrospray ionization mass spectrometer.

In some exemplary embodiments, the electrospray ionization mass spectrometer can be coupled online to a chromatographic system with a chromatography resin.

In some exemplary embodiments, the electrospray ionization mass spectrometer can be run under native conditions.

In some exemplary embodiments, the chromatographic system can be coupled to the electrospray ionization mass spectrometer using a splitter with at least three paths.

In some exemplary embodiments, the chromatographic system can be coupled to an ultraviolet detector using a splitter with at least three paths.

In some exemplary embodiments, the chromatographic system can be coupled to the electrospray ionization mass spectrometer and an ultraviolet detector using a splitter with at least three paths.

In some exemplary embodiments, the chromatographic system can be coupled to an electrospray ionization mass spectrometer and an ultraviolet detector using a splitter with at least three paths, wherein the electrospray ionization mass spectrometer is a nano-electrospray ionization mass spectrometer.

In some exemplary embodiments, the chromatographic system can be coupled to an electrospray ionization a mass spectrometer and an ultraviolet detector using a splitter with at least three paths, wherein the mass spectrometer can be electrospray ionization mass spectrometer operating under native conditions.

In some exemplary embodiments, the chromatographic system can be coupled to an electrospray ionization mass spectrometer and an ultraviolet detector using a splitter with at least three paths, wherein the electrospray ionization mass spectrometer can be a nano-electrospray ionization mass spectrometer under native conditions.

In some exemplary embodiments, the eluent including the protein or antigen-antibody complex or antibody-drug conjugate from washing the resin can be introduced in an ultraviolet detector through at least one splitter with at least three paths at a flow rate of about 0.2 mL/min to about 0.4 mL/min.

In some exemplary embodiments, the mobile phase for washing can have a flow rate of about 0.2 mL/min to about 0.4 mL/min.

In some exemplary embodiments, the mobile phase can comprise a volatile salt. In some specific embodiments, the mobile phase can comprise ammonium acetate, ammonium bicarbonate, or ammonium formate, or combinations thereof.

In some exemplary embodiments, the mobile phase used can be compatible with the mass spectrometer.

In some exemplary embodiments, the sample can comprise about 10 μg to about 100 μg of the dimer species.

In some exemplary embodiments, the flow rate in the electrospray ionization mass spectrometer can be about 10 nL/min to about 50 nL/min.

In some exemplary embodiments, the electrospray ionization mass spectrometer can have a spray voltage of about 0.8 kV to about 1.5 kV.

In some exemplary embodiments, identifying can include protein sequencing, protein de novo sequencing, identifying post-translational modifications, or comparability analysis, or combinations thereof.

In some exemplary embodiments, the sample can also comprise monomer of proteins.

In some exemplary embodiments, the dimer can comprise a first protein and a second protein, wherein the first protein and the second protein can be a therapeutic antibody, an antibody, a monoclonal antibody, a polyclonal antibody, a bispecific antibody, an antibody fragment, a fusion protein, or combinations thereof. In one aspect, the antibody fragment can include Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In some exemplary embodiments, the dimer species can be a product-related impurity present in a co-formulated preparation.

In some exemplary embodiments, the dimer can comprise a first protein and a second protein, wherein the first protein and the second protein can have a pI in the range of about 4.5 to about 9.0. In one aspect, the protein can have a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

It is understood that the methods are not limited to any of the aforesaid protein, impurity, and column and that the methods for identifying or quantifying may be conducted by any suitable means.

In some exemplary embodiments, this disclosure provides a system comprising a chromatographic column 100 having a chromatography resin, wherein the chromatographic column can be capable of receiving a mobile phase and a sample including a protein, and an electrospray ionization mass spectrometer 110 (See FIG. 1).

In some exemplary embodiments, the chromatographic column 100 can have a resin selected from hydrophobic interaction chromatography resin, anion exchange resin, anion exchange resin, affinity chromatography rein, size exclusion chromatography resin, a mixed mode resin, or combinations thereof.

In some exemplary embodiments, the electrospray ionization mass spectrometer 110 can be capable of being coupled to said chromatographic column 100.

In some exemplary embodiments, the electrospray ionization mass spectrometer 110 can be capable of being run under native conditions.

In some exemplary embodiments, the electrospray ionization mass spectrometer 110 can be a nano electrospray ionization mass spectrometer.

In some exemplary embodiments, the electrospray ionization mass spectrometer 110 can be a nano electrospray ionization mass spectrometer run under native conditions.

In some exemplary embodiments, the chromatographic column 100 can be capable of being coupled to the electrospray ionization mass spectrometer 100 using a splitter with at least three paths 120.

In some exemplary embodiments, the chromatographic column 100 can be capable of being coupled to an ultraviolet detector 130 using a splitter with at least three paths 120.

In some exemplary embodiments, the chromatographic column 100 can be capable of being coupled to an ultraviolet detector 130 and the electrospray ionization mass spectrometer 110 using a splitter with at least three paths 120.

In some exemplary embodiments, the three way splitter 120 can be capable of being disproportionately split to allow a flow from the chromatographic column 100 to an ultraviolet detector 130 and the electrospray ionization mass spectrometer 110.

In some exemplary embodiments, the system can be capable of identifying a dimer species.

An exemplary embodiment of the system in displayed in FIG. 1. A post-column splitter with at least three paths is used to enable UV/MS dual detection. The low volume fraction can be directed to the MS while the high volume fraction is transferred to the UV detector. Detection almost shares the same retention times. Fractions from the UV detector can be collected for sample recovery.

It is understood that the system is not limited to any of the aforesaid protein, chromatography column, mass spectrometer, antibody-drug conjugate, antigen-antibody complex.

This disclosure, at least in part, provides a method for quantifying a heterodimer species in a sample comprising a first protein and a second protein, said method comprising immobilizing an antibody specific to the first protein on a solid surface, incubating the sample with said antibody, capturing a precipitated sample, collecting a flow through, treating the precipitated sample with a first compound, treating the flow through with a second compound, mixing the treated precipitated sample and at least a portion of the treated flow through to form a mixture, and analyzing the mixture using a liquid chromatography coupled to a mass spectrometer to quantify the heterodimer species in the sample.

In some exemplary embodiments, the first protein can be an antibody, a bispecific antibody, a multispecific antibody, antibody fragment, monoclonal antibody, or an Fc fusion protein monoclonal antibody. In some exemplary embodiments, the first protein can be a monoclonal antibody.

In some exemplary embodiments, the second protein can an antibody, a bispecific antibody, a multispecific antibody, antibody fragment, monoclonal antibody, or a Fc fusion protein. In some exemplary embodiments, the first protein can be an Fc fusion protein.

In some embodiments, the sample comprising a first protein and a second protein can further comprise species selected from homodimer species of first protein, homodimer species of first protein, heterodimer species of first protein and second protein, or combinations thereof.

In some embodiments, the sample comprising a first protein and a second protein can further comprise at least one more protein.

In some embodiments, the solid surface can be selected from affinity resins, magnetic beads and coated plates. Non-limiting examples of affinity resins include protein A agarose beads, protein G agarose beads, protein A sepharose beads and protein G sepharose beads.

In some embodiments, the magnetic beads can have a monolayer of recombinant streptavidin covalently coupled to the surface.

In some embodiments, the antibody specific to the first protein on a solid surface and the sample can be incubated for several minutes to several hours.

In some embodiments, the precipitated sample can be obtained by centrifugation. In some specific embodiments, the flow through can be obtained by collecting the supernatant.

In some embodiments, the precipitated sample can be re-suspended by heating the re-suspended precipitated sample.

In some embodiments, the precipitated sample can be re-suspended by heating the re-suspended precipitated sample.

In some embodiments, the precipitated sample can undergo elution.

In some embodiments, the precipitated sample and flow through can be reduced by using a reducing agent. In some specific embodiments, the reducing agent can be dithiothreitol.

In some embodiments, the treatment can include alkylation.

In some embodiments, the first compound and the second compound can be isotopes.

In some exemplary embodiments, the at least a portion of the treated flow through can include about 10% of the treated flow through. In one aspect, the at least a portion of the treated flow through can ne about 1%, about 2%, about 3%, about 4%, about 5%, about 6%, about 7%, about 8%, about 9%, about 10%, about 15%, about 20%, about 20%, about 25%, about 30%, about 35%, about 40%, about 45%, about 50%, about 55%, about 60%, about 65%, about 70%, about 75%, about 80%, about 85%, about 90%, about 95%, about or 100%.

In some embodiments, the first compound and the second compound can be labeled iodoacetamide and unlabeled iodoacetamide respectively. In some other exemplary embodiments, the first compound and the second compound can be unlabeled iodoacetamide and labeled iodoacetamide respectively.

In some embodiments, the mixture can be digested before analyzing it using the liquid chromatography coupled to the mass spectrometer. In one aspect, the mixture can be digested using a hydrolyzing agent selected from trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus saitoi*.

In some embodiments, the mixture can be digested using trypsin.

In some embodiments, the mixture can be deglycosylated before analyzing it using the liquid chromatography coupled to the mass spectrometer.

Figure 4:
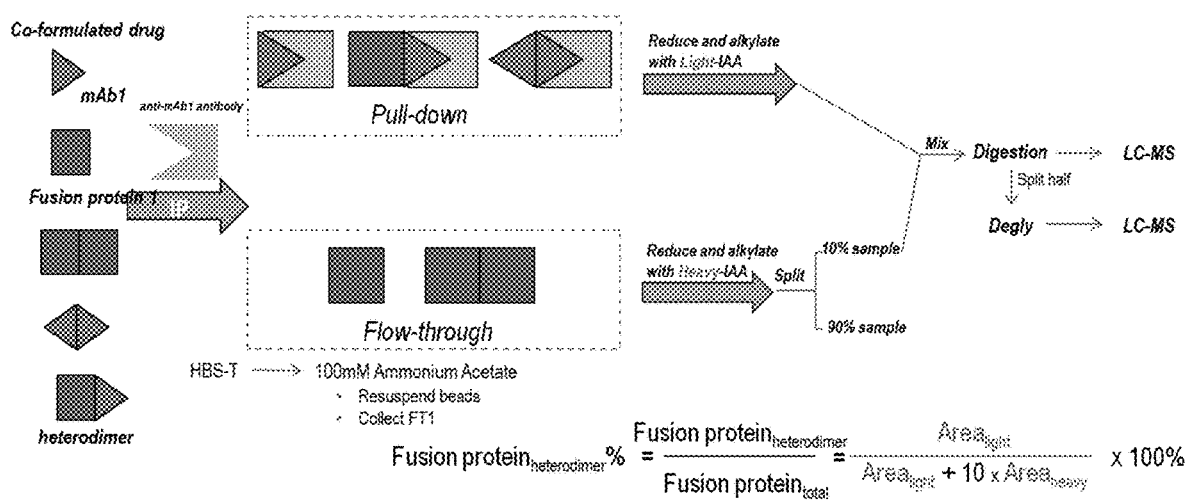
FIG. 4 shows an exemplary embodiment of the method used to quantify heterodimer species in a sample of a co-formulated preparation.

An example of one exemplary embodiment is represented in FIG. 4. As shown in FIG. 4, the mixture can be digested and then split into half. One half can be analyzed using the liquid chromatography coupled to the mass spectrometer and the other half can be deglycosylated and analyzed using the liquid chromatography coupled to the mass spectrometer.

In some embodiments, the liquid chromatography can be reversed-phased (RP), ion exchange (IEX), mixed mode chromatography and normal phase chromatography (NP).

In some exemplary embodiments, the mass spectrometer can be a tandem mass spectrometer.

In some exemplary embodiments, the mass spectrometer can be a electrospray mass spectrometer.

In some exemplary embodiments, the mass spectrometer can be a nano-electrospray mass spectrometer.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, digesting the mixture, and deglycosyalting the digested mixture.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, digesting the mixture, and analyzing the mixture using a liquid chromatography coupled to a mass spectrometer to quantify the heterodimer species in the sample.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and at least a portion of the treated flow through to form a mixture, digesting the mixture, deglycosyalting the digested mixture, and analyzing the mixture using a liquid chromatography coupled to a mass spectrometer to quantify the heterodimer species in the sample.

In some exemplary embodiments, the method for quantifying a heterodimer species in a sample comprising a first protein and a second protein can comprise analyzing using a liquid chromatography coupled to a mass spectrometer to quantify the heterodimer species in the sample, wherein the mass spectrometer can be a tandem mass spectrometer.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, and adding a reducing agent to the precipitated sample.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, and adding a reducing agent to the flow through.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and about 10% of the treated flow through to form a mixture, and analyzing the mixture using a liquid chromatography coupled to a mass spectrometer to quantify the heterodimer species in the sample.

In some exemplary embodiments, the method for quantifying a heterodimer species in a sample comprising a first protein and a second protein can comprise immobilizing an antibody specific to the first protein on a solid surface, capturing a precipitated sample and collecting a flow through, and treating the captured precipitated sample with a first compound and the flow through with a second compound, mixing the treated precipitated sample and about 10% of the treated flow through to form a mixture, digesting the mixture, and analyzing the mixture using a liquid chromatography coupled to a mass spectrometer to quantify the heterodimer species in the sample.

In some exemplary embodiment, the method for quantifying a heterodimer species in a sample can comprise a first protein and a second protein, wherein the sample can be stressed by subjecting it a condition selected from a group consisting of cool-white light exposure, hydrogen peroxide exposure, ultraviolet light exposure, heat, or combinations thereof, including forced degradation under ICH guidelines.

In some embodiments, the % second protein heterodimer in a sample comprising a first protein and a second protein, wherein the first protein is treated with an unlabeled compound and the second protein is treated with a labeled compound, can be calculated using the formula stated below:

$$\text{second protein heterodimer \%} = \frac{\text{amount of second protein as heterodimer}}{\text{total amount of second protein}} = \frac{\text{area light}}{\text{area light} + \text{area heavy}},$$

wherein area light is the area under the curve of MS peaks determine for the second protein treated with an unlabeled compound and area heavy is the area under the curve of MS peaks determine for the second protein treated with an labeled compound. The method can also be implemented such that the first protein is treated with a labeled compound and the second protein is treated with a unlabeled compound.

In some embodiments, the % second protein heterodimer in a sample comprising a first protein and a second protein, wherein the first protein is treated with an unlabeled compound and the second protein is treated with a labeled compound, can be calculated using the formula stated below:

$$\text{second protein heterodimer \%} = \frac{\text{amount of second protein as heterodimer}}{\text{total amount of second protein}} = \frac{\text{area light}}{\text{area light} + 10 \text{ (area heavy)}},$$

wherein area light is the area under the curve of MS peaks determine for the second protein treated with an unlabeled compound and area heavy is the area under the curve of MS peaks determine for the second protein treated with an labeled compound. The method can also be implemented such that the first protein is treated with a labeled compound and the second protein is treated with a unlabeled compound.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is herein incorporated by reference, in its entirety and for all purposes.

The disclosure will be more fully understood by reference to the following Examples, which are provided to describe the disclosure in greater detail. They are intended to illustrate examples and should not be construed as limiting the scope of the disclosure.

EXAMPLES

Materials and reagents. Water was purchased from Honeywell (Muskegon, MI). Ammonium acetate was purchased from Sigma-Aldrich (St Louis, MO). 1 M Tris-HCl, pH 7.5 was purchased from Teknova (Hollister, CA). Fused silica tubing (inner Diameter (ID) 150 µm, outer diameter (OD) 360 µm), 3-way connector and sleeve were purchased from IDEX (Oak Harbor, WA). PicoTip EMITTER SilicaTip (FS360-20-10-D-20-7CT) was purchased from New Objective (Woburn, MA). ACQUITY UPLC Protein BEH SEC Column, 200 Å, 1.7 µm, 4.6×300 mm was purchased from Waters (Milford, MA). Hot pocket column heater was purchased from Thermo-Fisher (Waltham, MA). All reagents were used without additional purification.

Online SEC-nano-ESI-MS analysis. ACQUITY UPLC I class system (Waters, Milford, MA) was coupled to Q Exactive HF hybrid quadrupole-Orbitrap mass spectrometer (Thermo Scientific, Bremen, Germany) for all online SEC-nano-ESI-MS analyses. ACQUITY UPLC Protein BEH SEC Column (200 Å, 1.7 µm, 4.6×300 mm) was set at 30° C. and used for mAbs and ADCs separation. Mobile phase was 100 mM ammonium acetate at pH 6.8. Each separation was 30 minutes with a flow rate of 0.3 mL/min, and the injection amount was set to 40 µg. A three-way splitter (T-splitter) was connected after the SEC column. Fused silica tubing (L: 140 cm, ID: 150 µm) and SilicaTip (L: 5 cm, ID: 10 µm) were connected to the T-splitter. The high volume fraction was transferred to the UV detector via fused silica tubing, while the low volume fraction was diverted to the MS via a SilicaTip. The following MS parameters were used for online SEC-nano-ESI-MS data acquisition. Each acquisition was 25 minutes beginning immediately after sample injection. Samples were ionized in positive mode with 3 kV spray voltage, 200° C. capillary temperature, and 70 S-lens RF level. In-source CID was set at 75 eV. Full MS scans were acquired at 15 K resolving power with mass range between m/z 2000-8000. A maximum injection time of 100 ms, automatic gain control target value of 3e6, and 10 microscans were used for full MS scans.

Data analysis. Protein Metrics Intact Mass software was used for raw data deconvolution. Thermo Xcalibur Qual Browser was used for extracted ion chromatogram analysis. Microsoft Excel was used for DAR calculation of ADCs.

Example 1

1.1 Online SEC-Nano-ESI-MS Instrumentation

SEC and MS technologies are routinely used for characterizing protein samples. SEC allows for the isolation and characterization of proteins under conditions that minimize changes in protein structure, while MS permits the identification of individual components in complex samples. Combining the individual capabilities of SEC and MS into a single platform would be highly desirable, but has proven challenging because the high flow rate and nonvolatile salts used for SEC analyses are incompatible with native MS. To overcome this limitation, reduction of solvent and salt intake into the MS by splitting the flow of eluate from the SEC using a post-column T-splitter was performed (See FIG. 1). The T-splitter was then connected to the MS via a SilicaTip and, in parallel, to a UV detector via fused silica tubing. This arrangement enabled simultaneous, dual UV/MS detection of SEC elutes. By varying the length and diameter of the fused silica tubing, flow rate to the MS via the SilicaTip could be regulated (e.g. longer/narrower tubing can generate higher resistance causing increased flow to the SilicaTip and MS). Protein samples were separated with a 4.6 mm SEC column using a 0.3 mL/min flow rate. The fused silica tubing connecting T-splitter and UV detector with a length of 140 cm and an inner diameter of 150 µm resulted in a desirable flow rate of ~1 µL/min to the SilicaTip. The length and diameter of the fused silica tubing also enabled near synchronous detection of molecules by the UV and MS.

1.2 Co-Formulated Preparation

Figure 5:
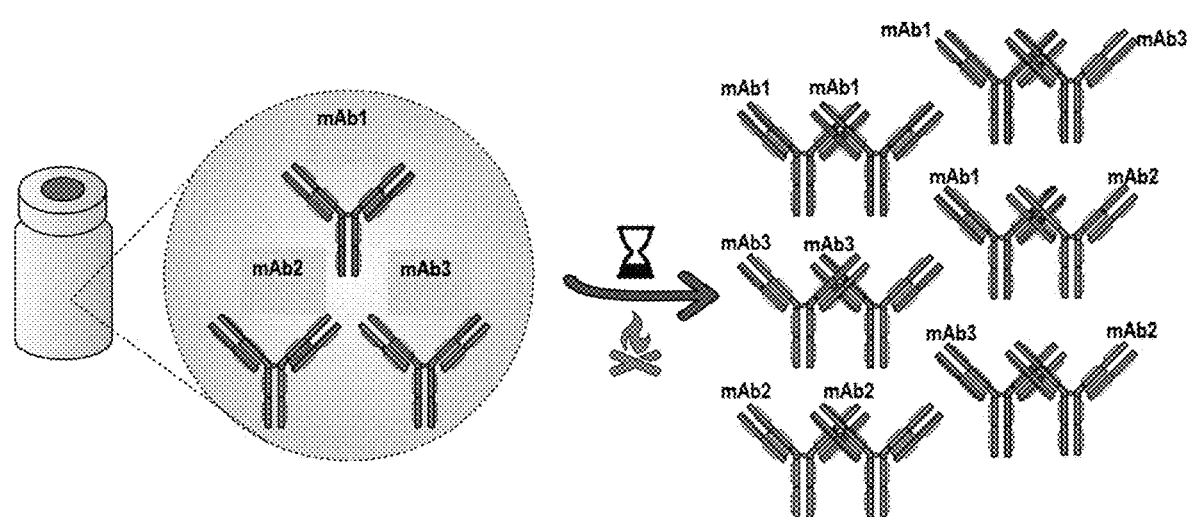
FIG. 5 shows the six dimers which may possibly be present in a co-formulation comprising three monoclonal antibodies.

A formulation comprising mAb1, mAb2, and mAb3 was used for the experiment. Six dimer species can be possibly present in the formulation (See FIG. 5). Samples were stressed under various conditions, including conditions provided in ICH guidelines such as photo stability testing (UV 1×ICH and CW 1×ICH).

1.3 Results

Figure 6:
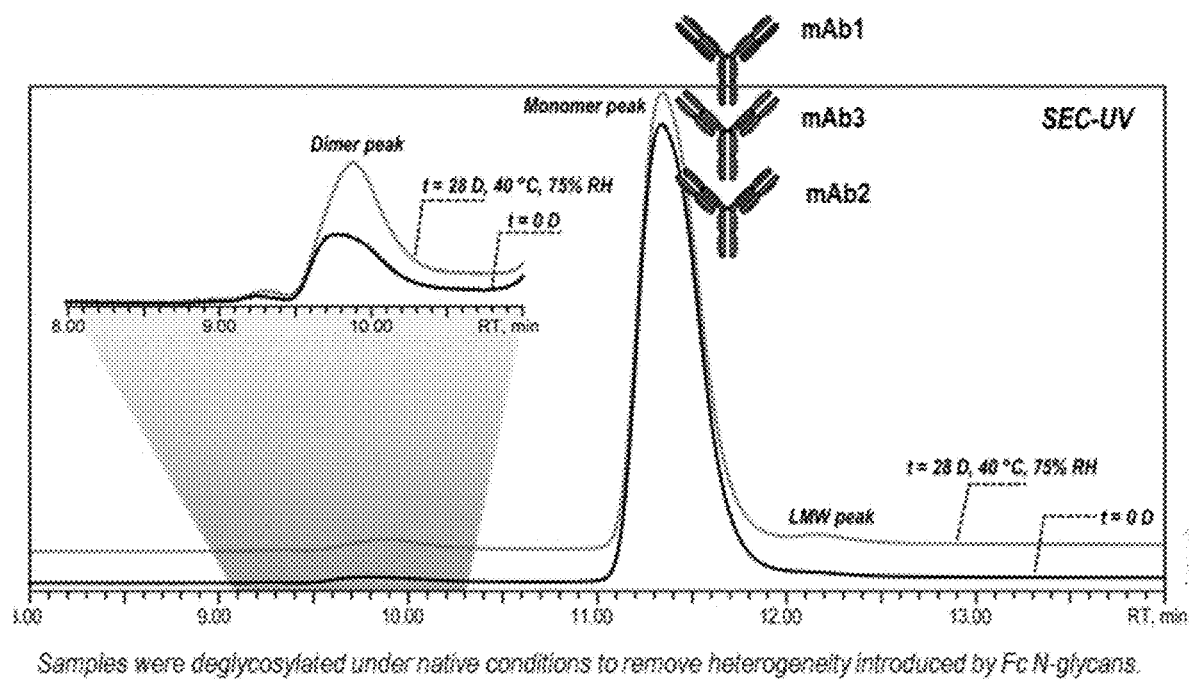
FIG. 6 shows identification of heterodimer species in a co-formulation comprising three monoclonal antibodies using native SEC-MS analysis according to an exemplary embodiment.
Figure 7:
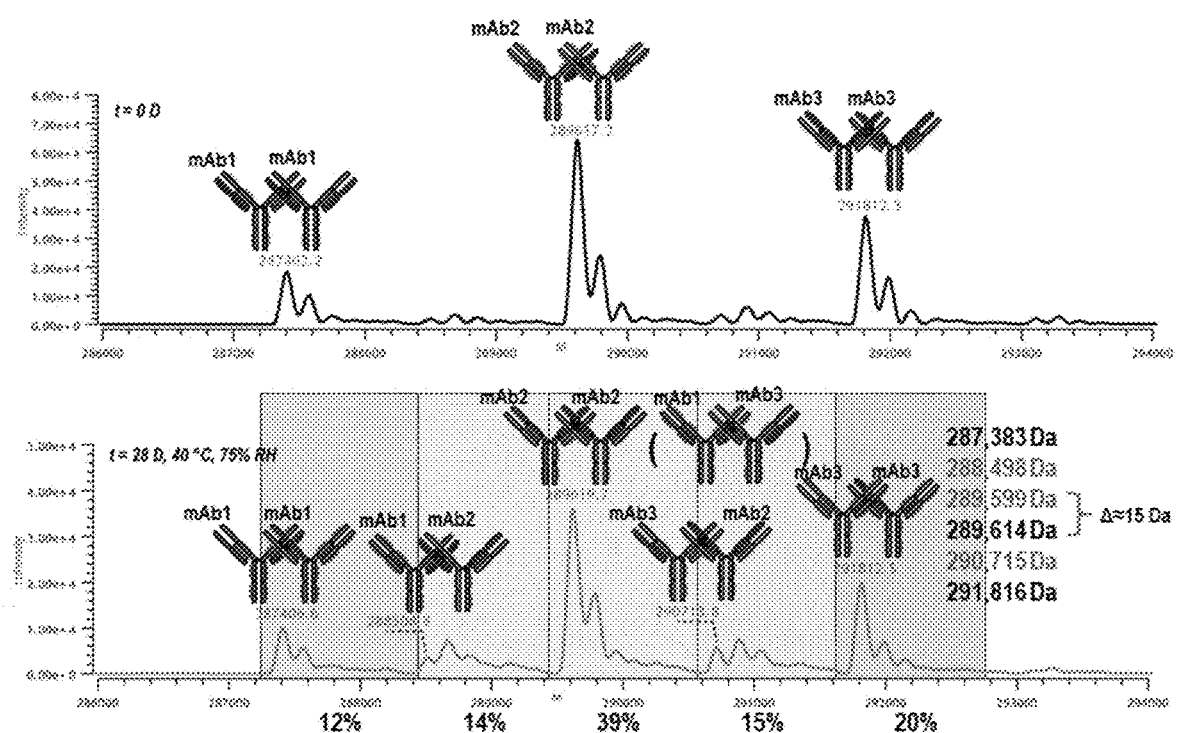
FIG. 7 shows quantification of heterodimer species in a co-formulation comprising three monoclonal antibodies using native SEC-MS analysis according to an exemplary embodiment.

Five dimers (mAb1-mAb1, mAb1-mAb2, mAb2-mAb2, mAb2-mAb3, and mAb3-mAb3) were successfully differentiated using the system illustrated in 1.1 using both the extracted ion chromatograms (XIC) and the molecular weight measurement as shown in FIGS. 6 and 7. The only heterodimer not identified was the mAb1-mAb3 since its molecular weight was very close to homodimer mAb2-mAb2 (different by 15 Da) (See FIG. 7).

Example 2

2.1 Online SEC-Nano-ESI-MS Instrumentation

The Instrumentation as Illustrated in 1.1 was Used.

2.2 Co-Formulated Preparation

Figure 8:
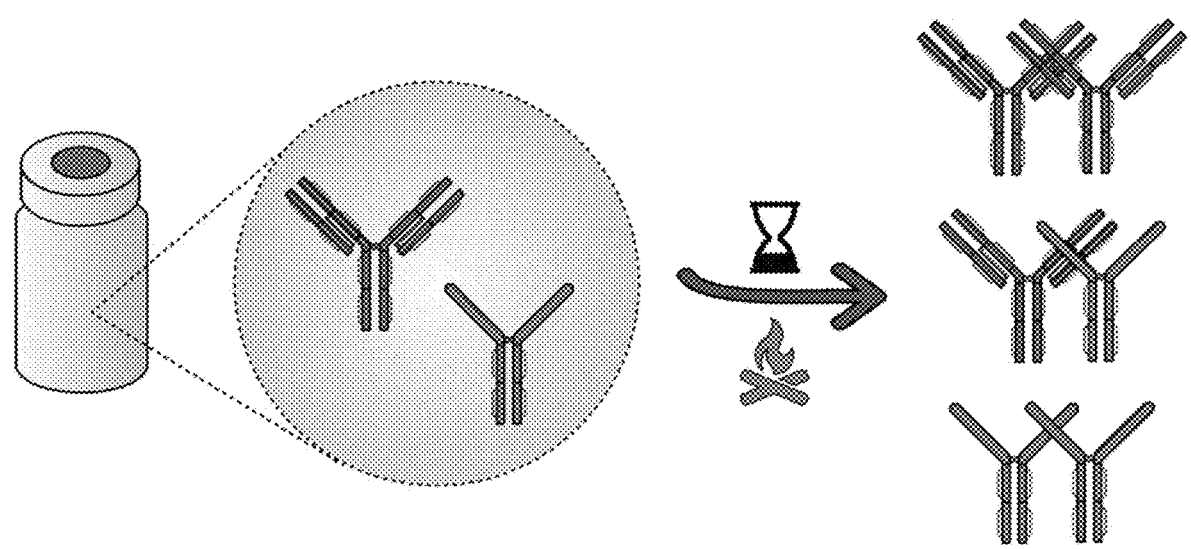
FIG. 8 shows the three dimers which may possibly be present in a co-formulation comprising a monoclonal antibody and a fusion protein.

A formulation comprising mAb1 and a fusion protein was used for the experiment. Three dimer species can be possibly present in the formulation (See FIG. 8). The presence of N-glycans in the fusion protein significantly complicates the intact mass analysis.

A co-formulation comprising mAb1 and fusion protein in the ratio of 120:40, a co-formulation comprising mAb1 and fusion protein in the ratio of 60:40, a formulation of mAb1 (120 mg/mL), a formulation of mAb1 (60 mg/mL), and a formulation of fusion protein (40 mg/mL), was subjected to four stress conditions: (a) cool-white light (CW), (b) hydrogen peroxide for 18 hours, (c) ultraviolet light (UV), and (d) heating at 37° C. for 28 hours. The stress conditions, included conditions provided by ICH guidelines.

The formulations and co-formulations subjected to the heating at 37° C. for 28 hours and treatment with hydrogen peroxide for 18 hours led to a mild increase in high molecular weight species (dimers or other aggregates). On the contrary, the formulations and co-formulations subjected treatment with cool-white light and ultraviolet light comprised high levels of high molecular weight species.

2.3 Identification of Dimer Species

Figure 9:
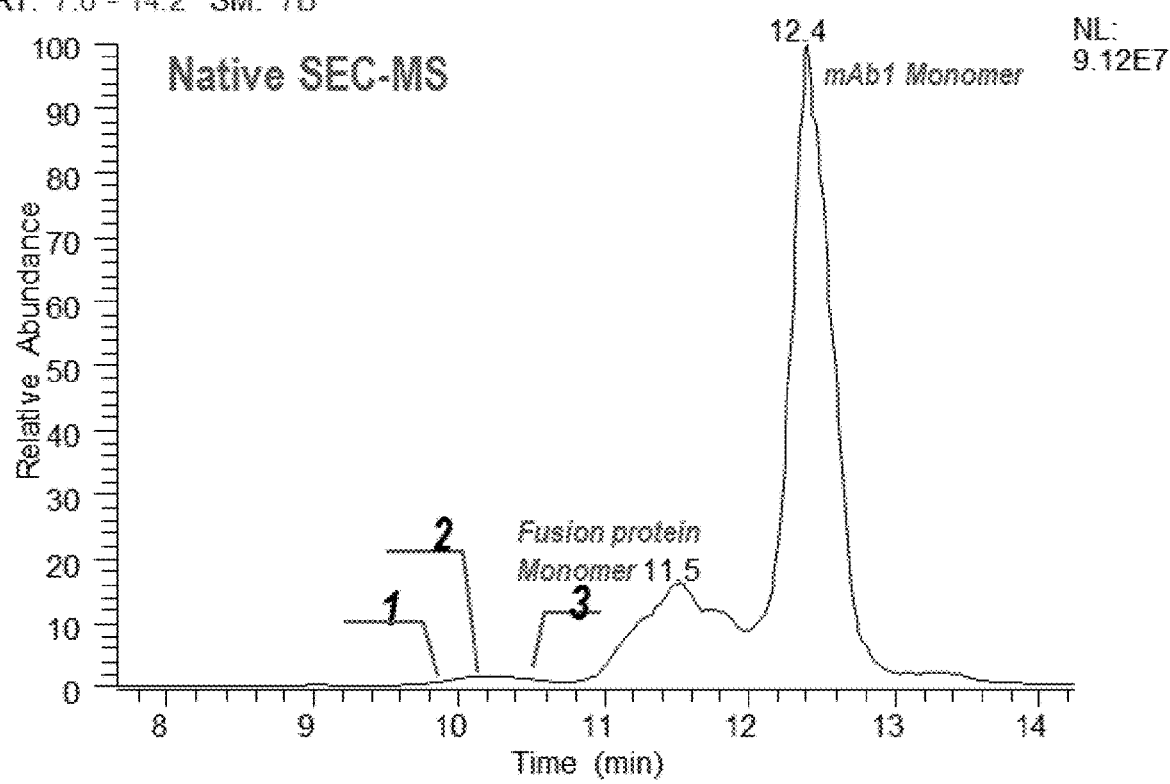
FIG. 9 shows an extracted ion chromatogram (XIC) of a co-formulation differentiated according to an exemplary embodiment.

The co-formulation comprising mAb1 and fusion protein in the ratio of 120:40 subjected to cool-white light was analyzed using the system illustrated in 1.1. FIG. 9 shows the extracted ion chromatogram (XIC) of the co-formulation analyzed using SEC-nano-ESI-MS. The method leads to differentiation of the monomer species and dimer species.

Figure 10:
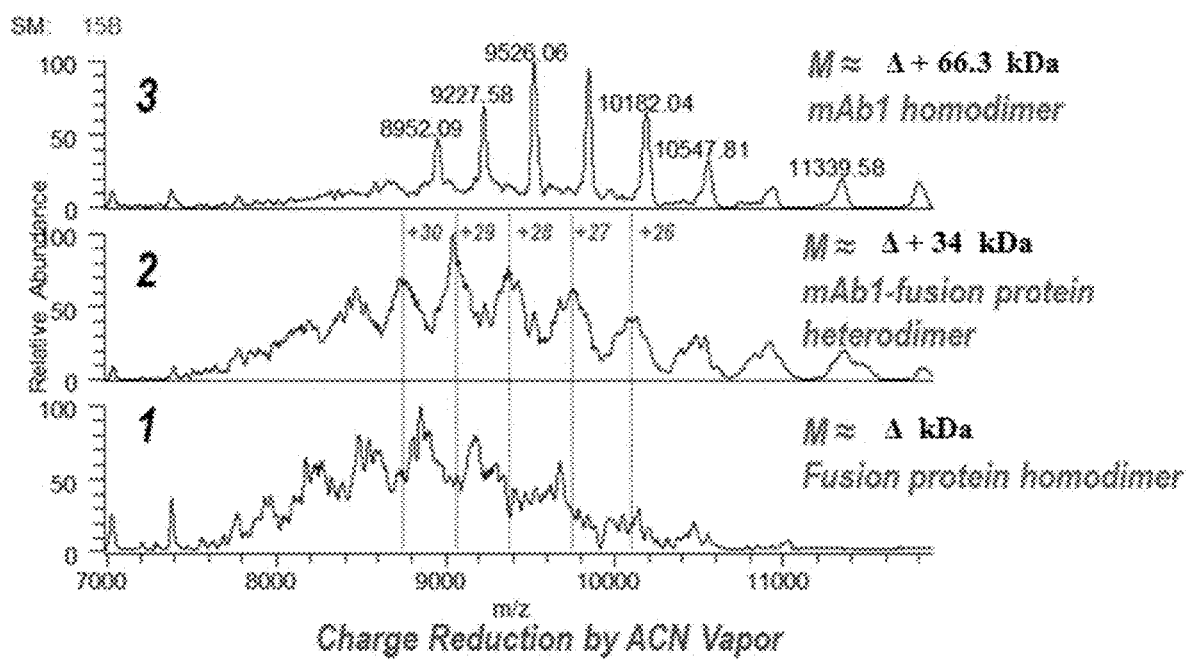
FIG. 10 shows mass to charge ratio determination of dimer species of a co-formulation differentiated according to an exemplary embodiment.

The application of charge reduction technique greatly improved the mass measurement of a protein ingredient that is highly heterogeneous in molecular weight as exemplified in FIG. 10.

An online SEC-nano-electrospray ionization (nano-ESI)-MS platform with dual ultraviolet (UV) and MS detection was developed. The utility of this platform was validated by identifying homodimer and heterodimer species in a co-formulated preparation.

The three way splitter was used to disproportionately split SEC eluates to a MS and UV detector, with the low-volume fraction directed to the MS and the high-volume fraction directed to the UV detector. The current platform enabled complementary dual detection by UV and native-MS, with the possibility of fraction collection, and can be applied to the characterization of dimer species. Further modifications to this online SEC-nano-ESI-MS platform, such as changing the column chemistry or using a Q Exactive UHMR instrument, would allow it to be adapted for other applications such as analyzing charge variants or very large protein complexes. The method described herein unlocked the possibility of combining high salt separation techniques (i.e. HIC, WCX) with mass spectrometry-based detection. In conclusion, the online SEC-nano-ESI-MS platform could be broadly applied to the analysis of protein biopharmaceuticals for a variety of applications.

Example 3

3.1 Sample Preparation

A co-formulation comprising mAb1 and fusion protein 1 was used. The different samples (50 μL) used for the experiment are illustrated in Table 1. The negative control (sample 3) was prepared by mixing the stressed fusion protein 1 (sample 1) and stressed mAb1 (sample 1) right before analysis, wherein the samples were stressed using ultraviolet light as provided under ICH guidelines. The other negative control (sample 7) was prepared by mixing the stressed fusion protein 1 (sample 6) and stressed mAb1 (sample 5) right before analysis, wherein the samples were stressed using cool-white light as provided under ICH guidelines.

10% Acetonitrile using a Thermomixer at 800 rpm. The beads were placed on the magnetic stand for 3 minutes to ensure that all of the beads are collected. The supernatant was removed between washes. This step was repeated three times (total 4 times). All of the supernatant was collected—1.2 mL of supernatant. In a 1.5 mL tube, mark as FT2; A 0.2 mL of elution buffer (50% ACN, 0.1% formic acid) was added and incubated at room temperature for 5 min on a Thermomixer at 1000 rpm. All the supernatant was collected into a tube and marked as PD-pull down.

3.3 Analysis

The analysis of the sample involved the following steps: Add 20 uL of 8 M urea in 100 mM Tris-HCl (pH 7.5) to each sample tube. Add 1 μL of 100 mM dithiothreitol (DTT) in Milli-Q water to each sample, vortex to mix well and incubate at 50° C. for 30 minutes. After incubation, add 1.1 uL of 200 mM light labeled iodoacetamide (light-IAA) in Milli-Q water to the pull down, and add 1.1 uL of 200 mM heavy labeled iodoacetamide (heavy-IAA) in Milli-Q water to the flow through. Incubate both pull down and flow through at room temperature in the dark for 30 minutes. Then, the entire pull down and about 10% of the flow through were mixed and digested by adding 4 μg of Trypsin and incubated for overnight at 37° C. The digested mixture was analyzed using LC-MS (Waters ACQUITY UPLC system and Thermo Q Exactive mass spectrometer).

Figure 13:
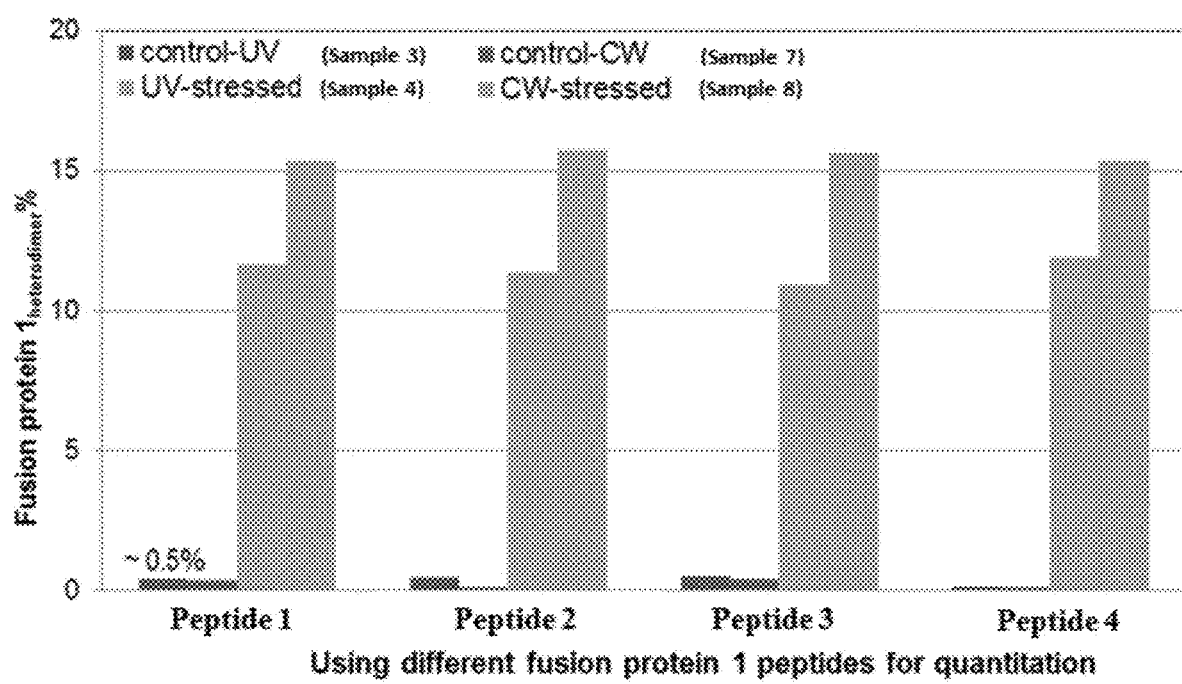
FIG. 13 shows a chart for fusion protein 1 heterodimer % in four peptides of fusion protein 1 found in samples stressed under different conditions, wherein the quantitation was performed according to an exemplary embodiment.
Figure 14:
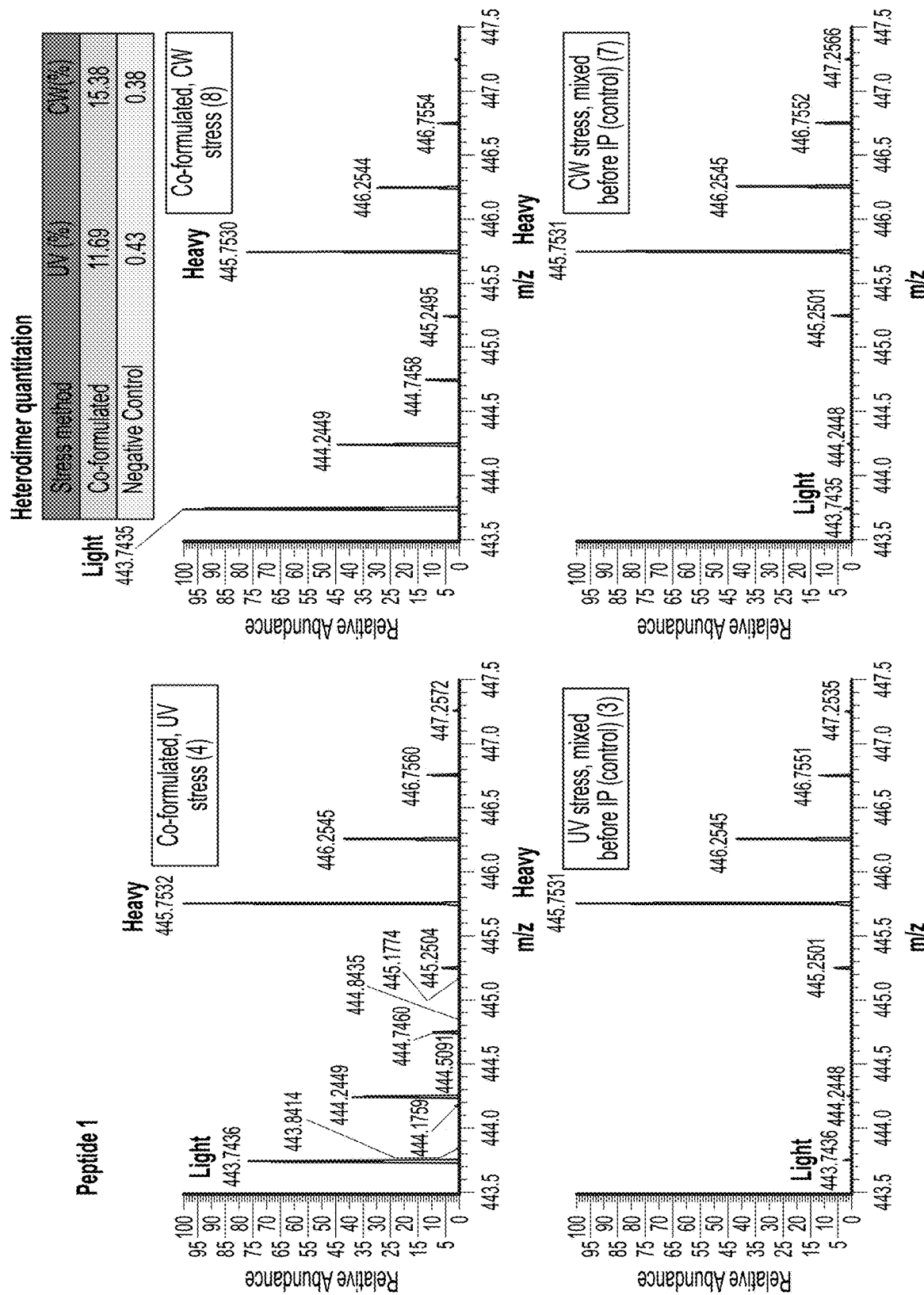
FIG. 14 shows chart of mass to charge ratio of fusion protein 1 peptide 1 (both light and heavy fragments) in samples stressed under different conditions, wherein the quantitation of a heterodimer comprising fusion protein 1 was performed according to an exemplary embodiment.
Figure 15:
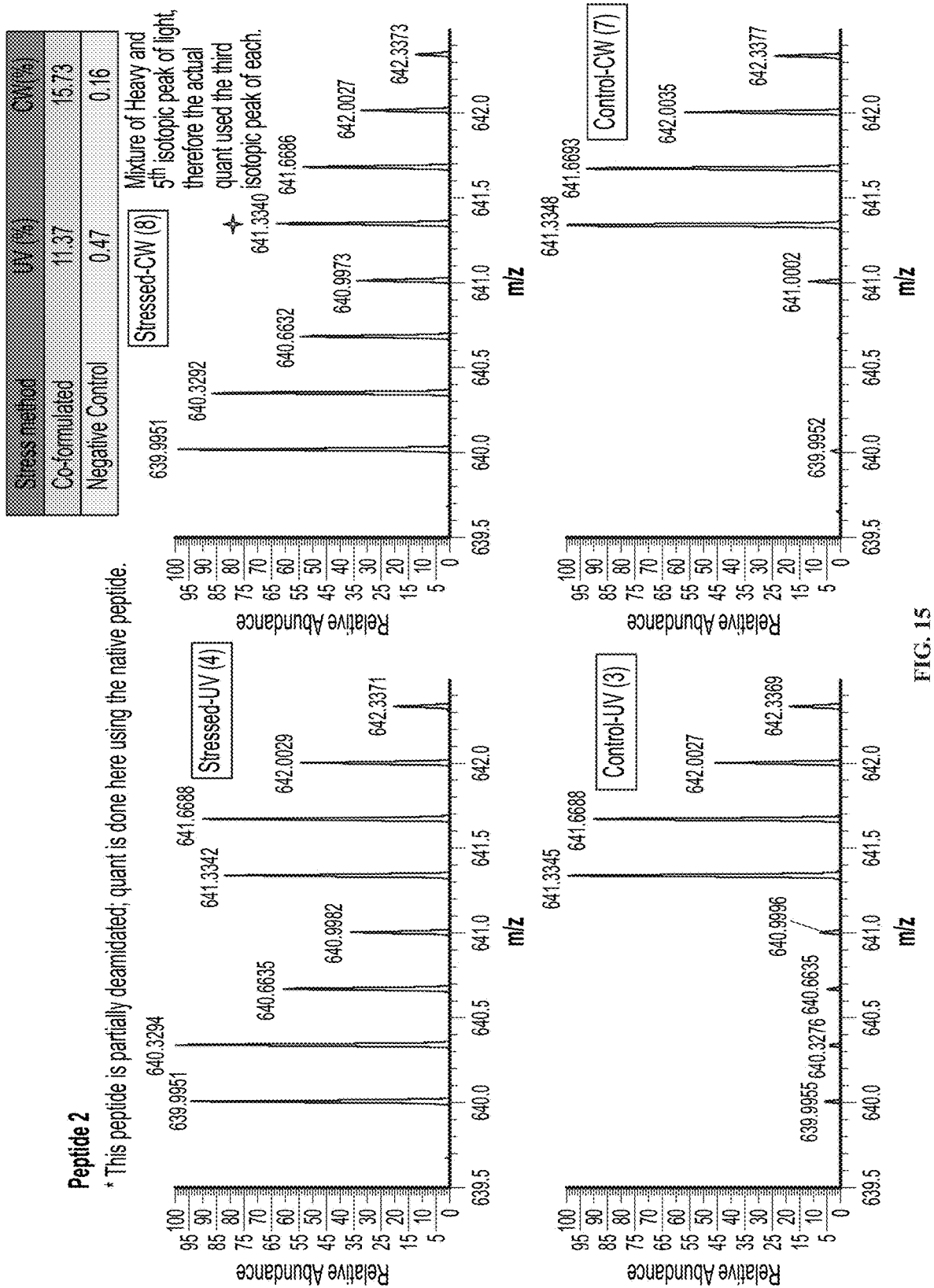
FIG. 15 shows chart of mass to charge ratio of fusion protein 1 peptide 2 (both light and heavy fragments) in samples stressed under different conditions, wherein the quantitation of a heterodimer comprising fusion protein 1 was performed according to an exemplary embodiment.
Figure 16:
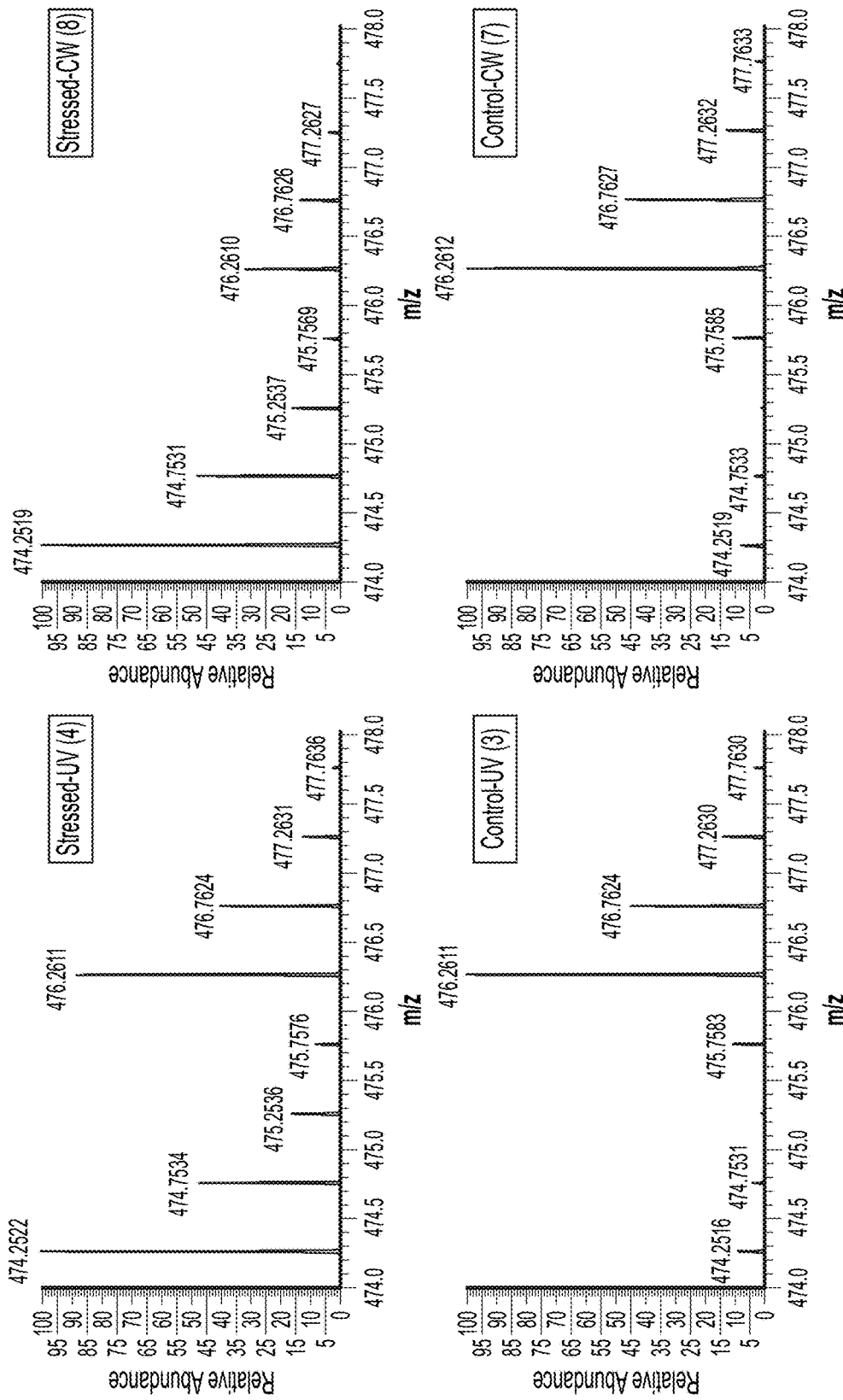
FIG. 16 shows chart of mass to charge ratio of fusion protein 1 peptide 3 (both light and heavy fragments) in samples stressed under different conditions, wherein the quantitation of a heterodimer comprising fusion protein 1 was performed according to an exemplary embodiment.
Figure 17:
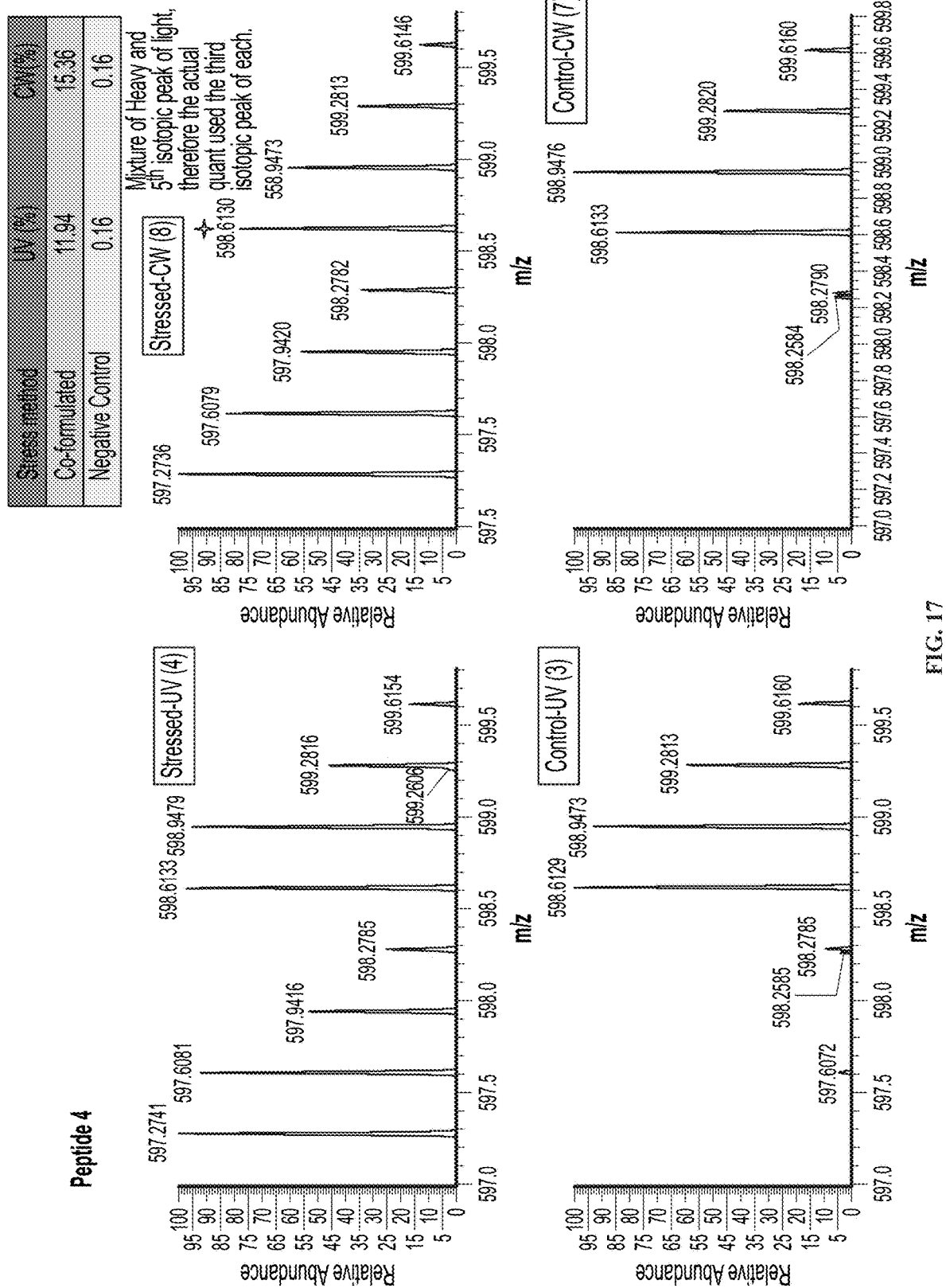
FIG. 17 shows chart of mass to charge ratio of fusion protein 1 peptide 4 (both light and heavy fragments) in samples stressed under different conditions, wherein the quantitation of a heterodimer comprising fusion protein 1 was performed according to an exemplary embodiment.

FIG. 12 shows the mass to charge ratios of the pull-down and flow-through obtained for samples 7 and 8. The pull-down fraction contains fusion protein 1 in heterodimer and flow-through fraction contains fusion protein 1 present in monomer and homodimer. FIG. 13 shows the calculated percentage of fusion protein 1 heterodimer. The calculation

TABLE 1

| Samples (stress conditions) | Conc. Info | % mAb1 Monomer | % fusion protein 1 Monomer | % Total Monomer | % HMW | % LMW |
|---|---|---|---|---|---|---|
| 1 mAb1 (UV) | mAb1 (120 mg/mL) | 80.25 | NA | 80.25 | 18.51 | 1.24 |
| 2 fusion protein 1 (UV) | fusion protein 1 (40 mg/mL) | NA | 81.03 | 81.03 | 18.97 | 0 |
| 3 Negative Control (UV) | Mixture of the above two | | | | | |
| 4 mAb1 + fusion protein 1 (UV) | 120:40, mAb1:fusion protein 1 | 67.64 | 14.75 | 82.39 | 16.63 | 0.98 |
| 5 mAb1 (CW) | mAb1 (120 mg/mL) | 73.75 | NA | 73.75 | 24.91 | 1.33 |
| 6 fusion protein 1 (CW) | fusion protein 1 (40 mg/mL) | NA | 81.78 | 81.78 | 18.23 | 0 |
| 7 Negative Control (CW) | Mixture of the above two | | | | | |
| 8 mAb1 + fusion protein 1 (CW) | 120:40, mAb1:fusion protein 1 | 62.01 | 12.87 | 74.88 | 24.15 | 0.99 |

3.2 Immunoprecipitation

Figure 11:
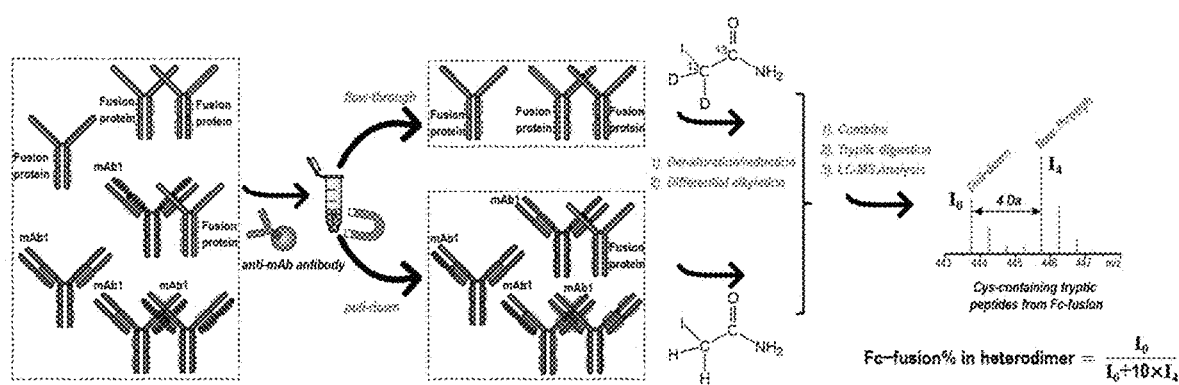
FIG. 11 shows a workflow of an immunoprecipation and isotope-labeling strategy for heterodimer quantitation according to an exemplary embodiment.

The immunoprecipitation was carried out as shown in FIG. 11. In six centrifugation tubes, 0.5 ml Dynabeads MyOne Streptavidin T1 (magnetic beads) and 100 μg Anti-mAb1 antibody was added. The samples 1, 2, 4, 5, 6, and 8 were added to individual tubes and incubated for 30 minutes at room temperature by gently mixing on a suitable shaker. The tubes were placed on a magnetic stand for 3 minutes to ensure that all of the beads are collected. The supernatant was removed and 0.4 mL of 100 mM of Ammonium acetate buffer was added. The tubes were incubated for 5 minutes on a Thermomixer at 800 rpm. This step was repeated twice (total 3 times). All the supernatant, 1.2 mL of supernatant, was collected in a 1.5 mL tube (and marked as FT1-flow through). The magnetic beads were washed with 0.4 mL was carried out using the formula shown in FIG. 4. For some of the peptides used to quantify the fusion protein 1, the mass to charge ratio charts in samples 3, 4, 7 and 8 are shown in FIGS. 14-17. The peptide 1, peptide 2, peptide 3, and peptide 4 in the figures represent peptide $^{25}$ELVIPCR$^{31}$, peptide $^{73}$EIGLLTCEATVNGHLYK$^{89}$, peptide $^{120}$LVLNCTAR$^{127}$, and peptide $^{178}$SDQGLYTCAASSGLMTK$^{194}$ respectively.

The % fusion protein 1 heterodimer was converted into heterodimer % by following the method as shown in FIG. 18. Based on the calculations for heterodimer % represented in FIG. 18, the heterodimer % in the sample 4 and sample 8 was found to be 6.4% and 8.5% respectively. The low levels of "heterodimer signal" from negative control samples (samples 3 and 7) could be attributed from interaction between mAb1 and fusion protein 1 after mixing and non-specific interaction between mAb1 and the affinity resin. The heterodimer % was consistent with the overall HMW %.

Example 4

To evaluate the quantitation limit and linearity of the fusion protein heterodimer by immunoprecipitation, samples with sequentially diluted cool-white stressed co-formulation preparation were used.

The testing samples prepared as listed in Table 2. A co-formulation comprising mAb1 and fusion protein 1 was used and stressed using a cool-white light. The negative control mixed sample was prepared by mixing the stressed fusion protein 1 (sample 6) and stressed mAb1 (sample 5) right before analysis. The different testing samples used for the experiment were prepared as illustrated in Table 2.

TABLE 2

| Tested Sample | Mix solutions | | |
|---|---|---|---|
| | Co-formulated-CW sample (μL) | Negative control Mixed sample (μL) | Final Volume |
| 1 Co-formulated-CW-1 | 20 | 0 | 20 |
| 2 Co-formulated-CW-½ | 10 | 10 | 20 |
| 3 Co-formulated-CW-¼ | 5 | 15 | 20 |
| 4 Co-formulated-CW-⅛ | 2.5 | 17.5 | 20 |
| 5 Co-formul ated-CW-1/16 | 1.25 | 18.75 | 20 |
| 6 Negative control | 0 | 20 | 20 |

Figure 19:
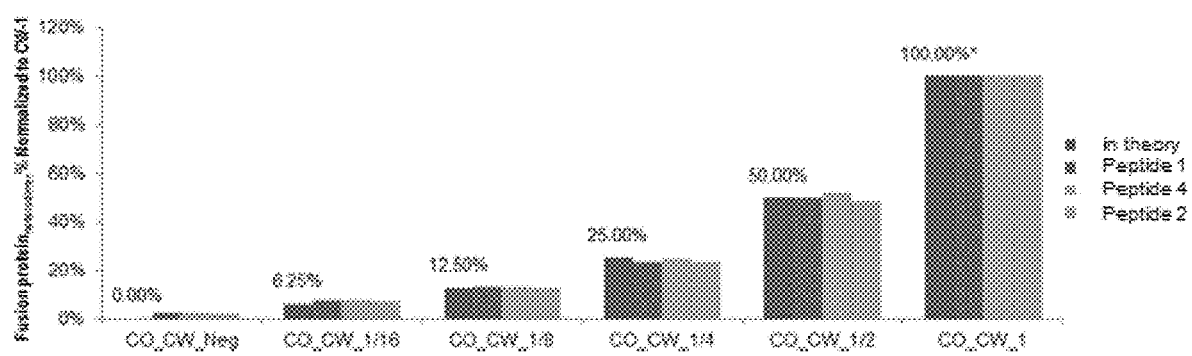
FIG. 19 represents a chart of fusion protein 1 heterodimer % in the tested samples normalized to fusion protein heterodimer % in the tested sample with no dilution, wherein the quantitation of a heterodimer comprising fusion protein 1 was performed according to an exemplary embodiment.
Figure 20:
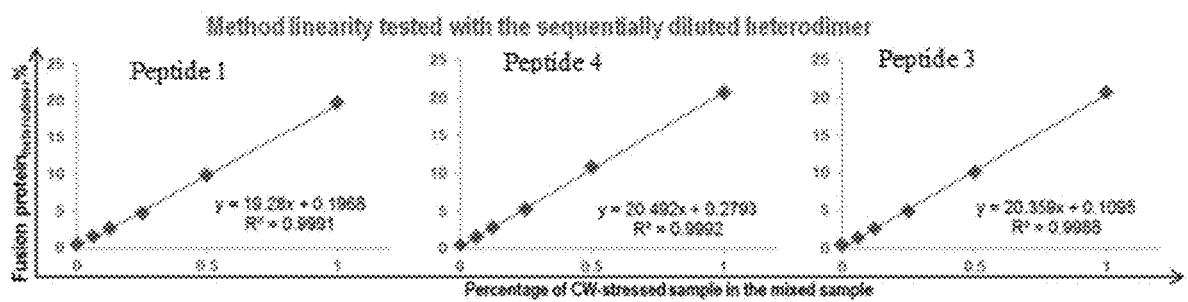
FIG. 20 shows a plot of fusion protein 1 heterodimer % vs. % cool-white stressed sample in the mixed sample for three of peptides used to quantify fusion protein 1, wherein the quantitation of a heterodimer comprising fusion protein 1 was performed according to an exemplary embodiment.

The immunoprecipitation and analysis was carried out as illustrated in 3.2 and 3.3. The chart of fusion protein heterodimer % in the tested samples normalized to fusion protein heterodimer % in the tested sample with no dilution is shown in FIG. 19. Further, the plot of fusion protein heterodimer % vs. % cool-white stressed sample in the mixed sample is shown in FIG. 20, for three of peptides used to quantify fusion protein 1, wherein the sample at dilution 1 represents the neat cool white-stressed co-formulated sample. The quantitation method maintained a good linearity at least as low as 0.8% of heterodimer (the lowest value tested).

Example 5

Figure 21:
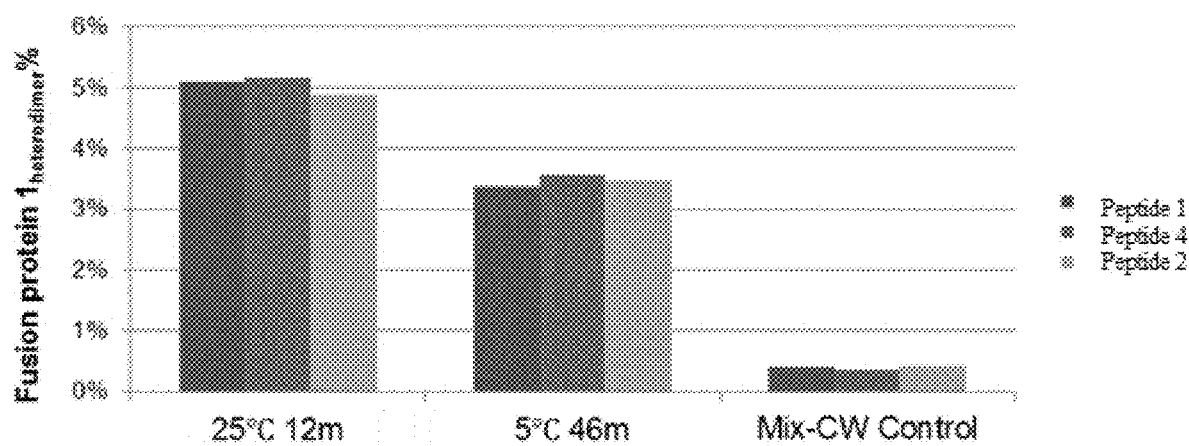
FIG. 21 shows the fusion protein 1 heterodimer % in samples from co-formulated preparations stored at ambient conditions, wherein the quantitation of a heterodimer comprising fusion protein 1 was performed according to an exemplary embodiment.

To evaluate the quantitation of heterodimer in ambient conditions stressed co-formulated samples, samples from a co-formulated preparation comprising mAb1 and fusion protein 1 were stored at 25° C. for 12 months and 5° C. for 46 months. The immunoprecipitation and analysis was carried out as illustrated in 3.2 and 3.3. The quantitation calculated in the samples is shown in Table 3 and FIG. 21, wherein the different fusion protein 1 peptides were used for quantitation.

TABLE 3

| Quantitation | 25° C. 12 m | 5° C. 46 m | Mix-CW (Negative Control) |
|---|---|---|---|
| ELVIPCR | 5.10% | 3.38% | 0.40% |
| SDQGLYTCAASSGLMTK | 5.18% | 3.56% | 0.36% |
| EIGLLTCEATVNGHLYK | 4.89% | 3.47% | 0.44% |
| Average$_{heterodimer}$ % | 5.06% | 3.47% | 0.40% |
| % heterodimer (Calculated) In UV Peak Areas | 2.78% | 1.91% | 0.22% |
| % HMW | 6.40% | 5.26% | |

Thus, a new immunoprecipitation method was developed for the quantitation of heterodimer level in samples obtained from co-formulated preparations. It was successfully applied to quantitate the level of heterodimer in both UV/CW stressed and ambient condition stressed samples from co-formulated preparations.

What is claimed is:

1. A method for identifying at least one dimer species, said method comprising:
    contacting a sample including the dimer species to a chromatographic system having a size-exclusion chromatography resin;
    washing said size-exclusion chromatography resin using a mobile phase to provide an eluent including the dimer species;
    identifying the dimer species in said eluent using an electrospray ionization mass spectrometer under native conditions, wherein at least one splitter with at least three paths is used to allow fluid communication between an ultraviolet detector to the chromatographic system having the size-exclusion chromatography resin; and
    wherein the eluent from washing the size-exclusion chromatography resin is introduced in the ultraviolet detector through the at least one splitter at a flow rate of about 0.2 mL/min to about 0.4 mL/min.

2. A method for identifying at least one dimer species, said method comprising:
    contacting a sample including the dimer species to a chromatographic system having a size-exclusion chromatography resin;
    washing said size-exclusion chromatography resin using a mobile phase to provide an eluent including the dimer species;
    identifying the dimer species in said eluent using an electrospray ionization mass spectrometer under native conditions; and
    wherein the mobile phase used to wash the size-exclusion chromatography resin comprises ammonium acetate.

3. A method for identifying at least one dimer species, said method comprising:
    contacting a sample including the dimer species to a chromatographic system having a size-exclusion chromatography resin;
    washing said size-exclusion chromatography resin using a mobile phase to provide an eluent including the dimer species;
    identifying the dimer species in said eluent using an electrospray ionization mass spectrometer under native conditions; and
    wherein the mobile phase used to wash the size-exclusion chromatography resin has a flow rate of about 0.2 mL/min to about 0.4 mL/min.

4. A method for identifying at least one dimer species, said method comprising:
    contacting a sample including the dimer species to a chromatographic system having a size-exclusion chromatography resin;

washing said size-exclusion chromatography resin using a mobile phase to provide an eluent including the dimer species;

identifying the dimer species in said eluent using an electrospray ionization mass spectrometer under native conditions; and wherein an amount of the sample including the dimer species contacted to the chromatography system is about 10 µg to about 100 µg.

5. A method for identifying at least one dimer species, said method comprising:

contacting a sample including the dimer species to a chromatographic system having a size-exclusion chromatography resin;

washing said size-exclusion chromatography resin using a mobile phase to provide an eluent including the dimer species;

identifying the dimer species in said eluent using an electrospray ionization mass spectrometer under native conditions; and wherein the eluent provided from washing the size-exclusion chromatography resin is introduced in the electrospray ionization mass spectrometer, wherein a flow rate of electrospray from the electrospray ionization is about 10 nL/min to about 50 nL/min.

6. A method for identifying at least one dimer species, said method comprising:

contacting a sample including the dimer species to a chromatographic system having a size-exclusion chromatography resin;

washing said size-exclusion chromatography resin using a mobile phase to provide an eluent including the dimer species;

identifying the dimer species in said eluent using an electrospray ionization mass spectrometer under native conditions; and wherein the eluent provided from washing the size-exclusion chromatography resin is introduced in the electrospray ionization mass spectrometer, wherein a spray voltage of electrospray is about 0.8 kV to about 1.5 kV.

7. A method for quantifying a heterodimer species in a sample comprising a first protein and a fusion protein, said method comprising:

immobilizing an antibody specific to the first protein on a solid surface;

incubating the sample with said antibody;

capturing a precipitated sample;

collecting a flow through;

treating the precipitated sample with a first compound;

treating the flow through with a second compound;

mixing the treated precipitated sample and at least a portion of the treated flow through to form a mixture; and analyzing the mixture using a liquid chromatography coupled to a mass spectrometer to quantify the heterodimer species in the sample, wherein the first compound is an isotope of the second compound; and wherein the first compound is iodoacetamide.

8. A method for quantifying a heterodimer species in a sample comprising a first protein and a fusion protein, said method comprising:

immobilizing an antibody specific to the first protein on a solid surface;

incubating the sample with said antibody;

capturing a precipitated sample;

collecting a flow through;

treating the precipitated sample with a first compound;

treating the flow through with a second compound;

mixing the treated precipitated sample and at least a portion of the treated flow through to form a mixture;

analyzing the mixture using a liquid chromatography coupled to a mass spectrometer to quantify the heterodimer species in the sample; and wherein the sample is stressed by subjecting it to a condition selected form a group consisting of cool-white light exposure, hydrogen peroxide exposure, ultraviolet light exposure, heat, or combinations thereof.

* * * * *